US010813564B2

(12) United States Patent
Rosen et al.

(10) Patent No.: US 10,813,564 B2
(45) Date of Patent: Oct. 27, 2020

(54) LOW FIELD MAGNETIC RESONANCE METHODS AND APPARATUS

(71) Applicant: Hyperfine Research, Inc., Guilford, CT (US)

(72) Inventors: Matthew Scot Rosen, Somerville, MA (US); Gregory L. Charvat, Guilford, CT (US); Laura Sacolick, Madison, CT (US); Mathieu Sarracanie, Somerville, MA (US); Jonathan M. Rothberg, Guilford, CT (US); Tyler S. Ralston, Clinton, CT (US)

(73) Assignee: Hyperfine Research, Inc., Guilford, CT (US)

( * ) Notice: Subject to any disclaimer, the term of this patent is extended or adjusted under 35 U.S.C. 154(b) by 1025 days.

(21) Appl. No.: 14/938,333

(22) Filed: Nov. 11, 2015

(65) Prior Publication Data

US 2016/0128592 A1     May 12, 2016

Related U.S. Application Data

(60) Provisional application No. 62/078,383, filed on Nov. 11, 2014.

(51) Int. Cl.
*A61B 5/04*     (2006.01)
*A61B 5/0476*     (2006.01)
(Continued)

(52) U.S. Cl.
CPC ........ *A61B 5/04012* (2013.01); *A61B 5/0402* (2013.01); *A61B 5/0476* (2013.01);
(Continued)

(58) Field of Classification Search
CPC ........ A61B 5/04012; A61B 2090/3954; A61B 5/055; G01R 33/445; G01R 33/3806; G01R 33/381
See application file for complete search history.

(56) References Cited

U.S. PATENT DOCUMENTS 3,622,869 A * 11/1971 Golay ............... G01R 33/3875
                                                 324/320
3,735,306 A      5/1973 Kabler et al.
(Continued)

FOREIGN PATENT DOCUMENTS

CN      1269512 A     10/2000
CN      1394550 A     2/2003
(Continued)

OTHER PUBLICATIONS

Hidalgo-Tobon, "Theory of Gradient Coil Design Methods for Magnetic Resonance Imaging" pp. 223-242, 2010 (Year: 2010).*
(Continued)

*Primary Examiner* — Bill Thomson
*Assistant Examiner* — Aminah Asghar
(74) *Attorney, Agent, or Firm* — Wolf, Greenfield & Sacks, P.C.

(57) ABSTRACT

According to some aspects a system is provided comprising a low-field magnetic resonance (MR) device, at least one electrophysiological device, and at least one controller configured to operate the low-field MR device to obtain MR data and to operate the at least one electrophysiological device to obtain electrophysiological data.

17 Claims, 12 Drawing Sheets

(51) Int. Cl.
  *A61B 5/00* (2006.01)
  *A61B 5/055* (2006.01)
  *G01R 33/38* (2006.01)
  *G01R 33/381* (2006.01)
  *A61B 5/0488* (2006.01)
  *A61B 5/0496* (2006.01)
  *A61B 5/0402* (2006.01)
  *G01R 33/48* (2006.01)
  *G01R 33/44* (2006.01)
  *A61B 90/00* (2016.01)

(52) U.S. Cl.
  CPC .......... *A61B 5/0488* (2013.01); *A61B 5/0496* (2013.01); *A61B 5/055* (2013.01); *A61B 5/7425* (2013.01); *G01R 33/3806* (2013.01); *G01R 33/445* (2013.01); *G01R 33/4808* (2013.01); *A61B 2090/3954* (2016.02); *A61B 2576/00* (2013.01); *G01R 33/381* (2013.01)

(56) References Cited

U.S. PATENT DOCUMENTS

| | | | |
|---|---|---|---|
| 4,595,899 A | 6/1986 | Smith et al. | |
| 4,621,299 A | 11/1986 | Hill | |
| 4,638,252 A | 1/1987 | Bradshaw | |
| 4,668,915 A | 5/1987 | Daubin et al. | |
| 4,675,609 A | 6/1987 | Danby et al. | |
| 4,770,182 A | 9/1988 | Damadian et al. | |
| 4,890,061 A | 12/1989 | Den Boef | |
| 4,893,082 A | 1/1990 | Letcher, III | |
| 5,047,720 A | 9/1991 | Guy | |
| 5,153,546 A | 10/1992 | Laskaris | |
| 5,194,810 A | 3/1993 | Breneman et al. | |
| 5,203,332 A | 4/1993 | Leunbach | |
| 5,252,924 A | 10/1993 | Sakurai et al. | |
| 5,382,904 A | 1/1995 | Pissanetzky | |
| 5,390,673 A | 2/1995 | Kikinis | |
| 5,423,315 A | 6/1995 | Margosian et al. | |
| 5,483,158 A | 1/1996 | Van Heteren et al. | |
| 5,490,509 A | 2/1996 | Carlson et al. | |
| 5,581,187 A * | 12/1996 | Pausch ................. | G01R 33/385 324/318 |
| 5,659,281 A | 8/1997 | Pissanetzky et al. | |
| 5,808,376 A | 9/1998 | Gordon et al. | |
| 5,864,236 A | 1/1999 | Li | |
| 6,037,850 A | 3/2000 | Honmei et al. | |
| 6,131,690 A | 10/2000 | Galando et al. | |
| 6,157,278 A | 12/2000 | Katznelson et al. | |
| 6,235,409 B1 | 5/2001 | Serafin et al. | |
| 6,262,576 B1 * | 7/2001 | Petropoulos ......... | G01R 33/385 324/318 |
| 6,267,830 B1 | 7/2001 | Groll | |
| 6,294,972 B1 | 9/2001 | Jesmanowicz et al. | |
| 6,317,618 B1 | 11/2001 | Livni et al. | |
| 6,362,620 B1 | 3/2002 | Debbins et al. | |
| 6,411,187 B1 | 6/2002 | Rotem et al. | |
| 6,452,472 B1 | 9/2002 | Aoki et al. | |
| 6,611,702 B2 | 8/2003 | Rohling et al. | |
| 6,677,752 B1 | 1/2004 | Creighton, IV et al. | |
| 6,819,108 B2 | 11/2004 | Huang et al. | |
| 7,019,610 B2 | 3/2006 | Creighton, IV et al. | |
| 7,116,102 B2 | 10/2006 | Clarke et al. | |
| 7,215,231 B1 | 5/2007 | Morrone | |
| 7,218,104 B2 | 5/2007 | Clarke et al. | |
| 7,239,143 B2 | 7/2007 | McBride | |
| 7,414,401 B1 | 8/2008 | Lvovsky | |
| 7,417,426 B2 | 8/2008 | Race et al. | |
| 7,538,553 B2 | 5/2009 | Trequattrini et al. | |
| 7,548,061 B2 | 6/2009 | Dewdney et al. | |
| 7,659,719 B2 | 2/2010 | Vaughan et al. | |
| 7,734,324 B2 | 6/2010 | Biglieri et al. | |
| 7,759,938 B2 | 7/2010 | Prado et al. | |
| 7,821,402 B2 | 10/2010 | Yang et al. | |
| 7,834,270 B2 | 11/2010 | Zhu et al. | |
| 7,966,059 B2 | 6/2011 | Creighton, IV et al. | |
| 8,049,504 B2 | 11/2011 | Findeklee | |
| 8,120,358 B2 | 2/2012 | Du | |
| 8,232,799 B2 | 7/2012 | Hajian et al. | |
| 8,335,359 B2 | 12/2012 | Fidrich et al. | |
| 8,368,402 B2 | 2/2013 | Lee et al. | |
| 8,378,682 B2 | 2/2013 | Subbarao | |
| 8,427,148 B2 | 4/2013 | O'Connor | |
| 8,451,004 B2 | 5/2013 | Walsh | |
| 8,570,042 B2 | 10/2013 | Pines et al. | |
| 8,614,575 B2 | 12/2013 | Demas et al. | |
| 8,699,199 B2 | 4/2014 | Blakes | |
| 8,901,928 B2 | 12/2014 | Alexiuk et al. | |
| 8,993,898 B2 | 3/2015 | Weibler et al. | |
| 9,222,998 B2 | 12/2015 | Teklemariam et al. | |
| 9,500,727 B2 | 11/2016 | Sohn et al. | |
| 9,500,731 B2 | 11/2016 | Castillo | |
| 9,541,616 B2 | 1/2017 | Rothberg et al. | |
| 9,547,057 B2 | 1/2017 | Rearick et al. | |
| 9,581,668 B2 | 2/2017 | Waddell | |
| 9,625,543 B2 | 4/2017 | Rearick et al. | |
| 9,625,544 B2 | 4/2017 | Poole et al. | |
| 9,638,773 B2 | 5/2017 | Poole et al. | |
| 9,645,210 B2 | 5/2017 | McNulty et al. | |
| 9,678,183 B2 | 6/2017 | Bulumulla et al. | |
| 9,797,971 B2 | 10/2017 | Rearick et al. | |
| 9,814,390 B2 | 11/2017 | Piron et al. | |
| 9,817,093 B2 | 11/2017 | Rothberg et al. | |
| 9,897,668 B2 | 2/2018 | Piron et al. | |
| 9,910,115 B2 | 3/2018 | Wald et al. | |
| 10,139,464 B2 | 11/2018 | Rearick et al. | |
| 10,145,913 B2 | 12/2018 | Hugon et al. | |
| 10,145,922 B2 | 12/2018 | Rothberg et al. | |
| 10,222,434 B2 | 3/2019 | Poole et al. | |
| 10,222,435 B2 | 3/2019 | Mileski et al. | |
| 10,241,177 B2 | 3/2019 | Poole et al. | |
| 10,274,561 B2 | 4/2019 | Poole et al. | |
| 10,281,540 B2 | 5/2019 | Mileski et al. | |
| 10,281,541 B2 | 5/2019 | Poole et al. | |
| 10,295,628 B2 | 5/2019 | Mileski et al. | |
| 10,310,037 B2 | 6/2019 | McNulty et al. | |
| 10,324,147 B2 | 6/2019 | McNulty et al. | |
| 10,330,755 B2 | 6/2019 | Poole et al. | |
| 10,353,030 B2 | 7/2019 | Poole et al. | |
| 10,371,773 B2 | 8/2019 | Poole et al. | |
| 10,379,186 B2 | 8/2019 | Rothberg et al. | |
| 10,416,264 B2 | 9/2019 | Sofka et al. | |
| 10,444,310 B2 | 10/2019 | Poole et al. | |
| 10,466,327 B2 | 11/2019 | Rothberg et al. | |
| 10,488,482 B2 | 11/2019 | Rearick et al. | |
| 10,495,712 B2 | 12/2019 | Rothberg et al. | |
| 10,520,566 B2 | 12/2019 | Poole et al. | |
| 10,527,692 B2 | 1/2020 | McNulty et al. | |
| 10,534,058 B2 | 1/2020 | Sofka et al. | |
| 10,539,637 B2 | 1/2020 | Poole et al. | |
| 10,545,207 B2 | 1/2020 | Poole et al. | |
| 10,551,452 B2 | 2/2020 | Rearick et al. | |
| 10,564,239 B2 | 2/2020 | Poole et al. | |
| 2002/0000806 A1 | 1/2002 | Nakamura et al. | |
| 2002/0050895 A1 | 5/2002 | Zuk et al. | |
| 2002/0175792 A1 | 11/2002 | Laskaris et al. | |
| 2004/0097802 A1 | 5/2004 | Cohen | |
| 2004/0251901 A1 | 12/2004 | Tsuda et al. | |
| 2005/0021019 A1 | 1/2005 | Hashimshony et al. | |
| 2005/0218896 A1 | 10/2005 | Gortler | |
| 2006/0052687 A1 | 3/2006 | Ruohonen | |
| 2006/0077027 A1 | 4/2006 | Aoki | |
| 2006/0186884 A1 | 8/2006 | Mallett et al. | |
| 2006/0241333 A1 | 10/2006 | Hunter | |
| 2007/0120631 A1 | 5/2007 | Hobbs et al. | |
| 2007/0216413 A1 | 9/2007 | Legall et al. | |
| 2007/0244385 A1 | 10/2007 | Satragno et al. | |
| 2007/0252595 A1 * | 11/2007 | Volegov ................ | A61B 5/055 324/307 |
| 2007/0257800 A1 | 11/2007 | Yang et al. | |
| 2007/0285197 A1 | 12/2007 | Shi et al. | |
| 2008/0084209 A1 | 4/2008 | Seeber et al. | |
| 2008/0258728 A1 | 10/2008 | Vernickel et al. | |
| 2009/0012387 A1 | 1/2009 | Hanson et al. | |

(56) References Cited

U.S. PATENT DOCUMENTS

| | | |
|---|---|---|
| 2009/0076377 A1 | 3/2009 | Findekelee |
| 2009/0099444 A1 | 4/2009 | Bogdanov |
| 2009/0138058 A1 | 5/2009 | Cooke et al. |
| 2009/0167304 A1 | 7/2009 | Prado et al. |
| 2010/0000780 A1 | 1/2010 | Zhu et al. |
| 2010/0056897 A1* | 3/2010 | Zhang .................. A61B 6/541 600/407 |
| 2010/0160817 A1 | 6/2010 | Parihar et al. |
| 2010/0219833 A1 | 9/2010 | McGinley et al. |
| 2010/0302701 A1 | 12/2010 | Olliges |
| 2010/0312095 A1 | 12/2010 | Jenkins et al. |
| 2011/0007445 A1 | 1/2011 | Blakes |
| 2011/0025332 A1 | 2/2011 | Abele et al. |
| 2011/0037467 A1 | 2/2011 | Tsuda |
| 2011/0088940 A1 | 4/2011 | Nordling et al. |
| 2011/0109311 A1 | 5/2011 | Walsh |
| 2011/0115485 A1 | 5/2011 | Subbarao |
| 2011/0199086 A1 | 8/2011 | Tsuda et al. |
| 2011/0210731 A1 | 9/2011 | Walsh |
| 2011/0210739 A1 | 9/2011 | Ham |
| 2011/0248715 A1 | 10/2011 | Telemariam et al. |
| 2012/0003160 A1* | 1/2012 | Wolf .................. A61B 5/0515 424/9.32 |
| 2012/0032767 A1 | 2/2012 | Iwasaki et al. |
| 2012/0092009 A1 | 4/2012 | Zhang et al. |
| 2012/0196753 A1 | 8/2012 | Laskaris et al. |
| 2012/0240385 A1 | 9/2012 | Teklemariam et al. |
| 2012/0268117 A1 | 10/2012 | Romano et al. |
| 2012/0296195 A1 | 11/2012 | Abbott et al. |
| 2012/0296197 A1 | 11/2012 | Vahala et al. |
| 2012/0323110 A1 | 12/2012 | Blake et al. |
| 2013/0035587 A1 | 2/2013 | Lagendijk et al. |
| 2013/0072780 A1 | 3/2013 | Espy et al. |
| 2013/0116544 A1 | 5/2013 | Rey et al. |
| 2013/0214612 A1 | 8/2013 | Bae |
| 2013/0271142 A1 | 10/2013 | Penanen et al. |
| 2013/0278255 A1 | 10/2013 | Khalighi et al. |
| 2013/0285659 A1 | 10/2013 | Sohn et al. |
| 2014/0066739 A1* | 3/2014 | He ..................... A61B 5/0042 600/377 |
| 2014/0111202 A1 | 4/2014 | Wald et al. |
| 2014/0128722 A1 | 5/2014 | Schweitzer et al. |
| 2014/0155732 A1 | 6/2014 | Patz et al. |
| 2014/0232402 A1 | 8/2014 | Tsuda |
| 2014/0275953 A1 | 9/2014 | Gregerson et al. |
| 2014/0341456 A1* | 11/2014 | Rodriguez ............ G06T 15/08 382/131 |
| 2014/0347053 A1 | 11/2014 | Dempsey et al. |
| 2015/0141799 A1 | 5/2015 | Rapoport et al. |
| 2015/0177343 A1 | 6/2015 | Wald et al. |
| 2015/0230810 A1 | 8/2015 | Creighton et al. |
| 2015/0253401 A1 | 9/2015 | Rapoport |
| 2015/0285882 A1 | 10/2015 | Mezrich et al. |
| 2015/0301134 A1 | 10/2015 | Hoshino et al. |
| 2015/0342177 A1 | 12/2015 | Hassanein et al. |
| 2016/0011290 A1 | 1/2016 | Iannello |
| 2016/0069968 A1 | 3/2016 | Rothberg et al. |
| 2016/0069970 A1 | 3/2016 | Rearick et al. |
| 2016/0069971 A1 | 3/2016 | McNulty et al. |
| 2016/0069972 A1 | 3/2016 | Poole et al. |
| 2016/0069975 A1 | 3/2016 | Rothberg et al. |
| 2016/0131727 A1 | 5/2016 | Sacolick et al. |
| 2016/0169992 A1 | 6/2016 | Rothberg et al. |
| 2016/0169993 A1 | 6/2016 | Rearick et al. |
| 2016/0187436 A1 | 6/2016 | Piron et al. |
| 2016/0223631 A1 | 8/2016 | Poole et al. |
| 2016/0231399 A1 | 8/2016 | Rothberg et al. |
| 2016/0231402 A1 | 8/2016 | Rothberg et al. |
| 2016/0231403 A1 | 8/2016 | Rothberg et al. |
| 2016/0231404 A1 | 8/2016 | Rothberg et al. |
| 2016/0299203 A1 | 10/2016 | Mileski et al. |
| 2016/0334479 A1 | 11/2016 | Poole et al. |
| 2016/0354058 A1 | 12/2016 | Schlosser et al. |
| 2016/0356869 A1 | 12/2016 | Dempsey et al. |
| 2017/0007148 A1 | 1/2017 | Kaditz et al. |
| 2017/0011255 A1 | 1/2017 | Kaditz et al. |
| 2017/0038451 A1 | 2/2017 | Ristic et al. |
| 2017/0102443 A1 | 4/2017 | Rearick et al. |
| 2017/0227616 A1 | 8/2017 | Poole et al. |
| 2017/0276747 A1 | 9/2017 | Hugon et al. |
| 2017/0276749 A1 | 9/2017 | Hugon et al. |
| 2017/0285122 A1 | 10/2017 | Kaditz et al. |
| 2017/0363700 A1 | 12/2017 | Gall et al. |
| 2018/0024208 A1 | 1/2018 | Rothberg et al. |
| 2018/0038931 A1 | 2/2018 | Rearick et al. |
| 2018/0088193 A1 | 3/2018 | Rearick et al. |
| 2018/0136292 A1 | 5/2018 | Piron et al. |
| 2018/0143274 A1 | 5/2018 | Poole et al. |
| 2018/0143275 A1 | 5/2018 | Sofka et al. |
| 2018/0143280 A1 | 5/2018 | Dyvorne et al. |
| 2018/0143281 A1 | 5/2018 | Sofka et al. |
| 2018/0144467 A1 | 5/2018 | Sofka et al. |
| 2018/0156881 A1 | 6/2018 | Poole et al. |
| 2018/0164390 A1 | 6/2018 | Poole et al. |
| 2018/0168527 A1 | 6/2018 | Poole et al. |
| 2018/0210047 A1 | 7/2018 | Poole et al. |
| 2018/0224512 A1 | 8/2018 | Poole et al. |
| 2018/0238978 A1 | 8/2018 | McNulty et al. |
| 2018/0238980 A1 | 8/2018 | Poole et al. |
| 2018/0238981 A1 | 8/2018 | Poole et al. |
| 2019/0004130 A1 | 1/2019 | Poole et al. |
| 2019/0011510 A1 | 1/2019 | Hugon et al. |
| 2019/0011513 A1 | 1/2019 | Poole et al. |
| 2019/0011514 A1 | 1/2019 | Poole et al. |
| 2019/0011521 A1 | 1/2019 | Sofka et al. |
| 2019/0018094 A1 | 1/2019 | Mileski et al. |
| 2019/0018095 A1 | 1/2019 | Mileski et al. |
| 2019/0018096 A1 | 1/2019 | Poole et al. |
| 2019/0025389 A1 | 1/2019 | McNulty et al. |
| 2019/0033402 A1 | 1/2019 | McNulty et al. |
| 2019/0033414 A1 | 1/2019 | Sofka et al. |
| 2019/0033415 A1 | 1/2019 | Sofka et al. |
| 2019/0033416 A1 | 1/2019 | Rothberg et al. |
| 2019/0038233 A1 | 2/2019 | Poole et al. |
| 2019/0086497 A1 | 3/2019 | Rearick et al. |
| 2019/0101607 A1 | 4/2019 | Rothberg et al. |
| 2019/0162806 A1 | 5/2019 | Poole et al. |
| 2019/0178962 A1 | 6/2019 | Poole et al. |
| 2019/0178963 A1 | 6/2019 | Poole et al. |
| 2019/0227136 A1 | 7/2019 | Mileski et al. |
| 2019/0227137 A1 | 7/2019 | Mileski et al. |
| 2019/0250227 A1 | 8/2019 | McNulty et al. |
| 2019/0250228 A1 | 8/2019 | McNulty et al. |
| 2019/0257903 A1 | 8/2019 | Poole et al. |
| 2019/0324098 A1 | 10/2019 | McNulty et al. |
| 2019/0353720 A1 | 11/2019 | Dyvorne et al. |
| 2019/0353723 A1 | 11/2019 | Dyvorne et al. |
| 2019/0353726 A1 | 11/2019 | Poole et al. |
| 2019/0353727 A1 | 11/2019 | Dyvorne et al. |
| 2020/0011952 A1 | 1/2020 | Rothberg et al. |
| 2020/0018806 A1 | 1/2020 | Rothberg et al. |
| 2020/0022611 A1 | 1/2020 | Nelson et al. |
| 2020/0022612 A1 | 1/2020 | McNulty et al. |
| 2020/0022613 A1 | 1/2020 | Nelson et al. |
| 2020/0025846 A1 | 1/2020 | Nelson et al. |
| 2020/0025851 A1 | 1/2020 | Rearick et al. |
| 2020/0033431 A1 | 1/2020 | Schlemper et al. |
| 2020/0034998 A1 | 1/2020 | Schlemper et al. |
| 2020/0041588 A1 | 2/2020 | O'Halloran et al. |
| 2020/0045112 A1 | 2/2020 | Sacolick et al. |
| 2020/0058106 A1 | 2/2020 | Lazarus et al. |

FOREIGN PATENT DOCUMENTS

| | | |
|---|---|---|
| CN | 101162637 A | 4/2008 |
| CN | 102713465 A | 10/2012 |
| CN | 103747726 A | 4/2014 |
| EP | 1262786 A2 | 12/2002 |
| EP | 1262786 A3 | 1/2003 |
| EP | 2418516 A2 | 2/2012 |
| TW | 389688 B | 5/2000 |
| TW | 570771 B | 1/2004 |
| WO | WO 2008/008447 A2 | 1/2008 |
| WO | WO 2009/042131 A1 | 4/2009 |

(56) References Cited

FOREIGN PATENT DOCUMENTS

| WO | WO 2013/016639 A1 | 1/2013 |
|---|---|---|
| WO | WO 2014/013257 A1 | 1/2014 |
| WO | WO 2014/102215 A1 | 7/2014 |
| WO | WO 2016/183284 A1 | 11/2016 |

OTHER PUBLICATIONS

International Search Report and Written Opinion dated Jan. 12, 2016 in connection with International Application No. PCT/US2015/060079.
Acar et al., Effects of Forward Model Errors on EEG Source Localization. Brain Topogr. 2013;23:378-96.
Makeig, Mind Monitoring via Mobile Brain-body Imaging. HCI. 2009;16:749-59.
Extended European Search Report for European Application No. 15837569.1 dated Apr. 6, 2018.
Extended European Search Report for European Application No. 15838192.1 dated Apr. 4, 2018.
International Search Report and Written Opinion for International Application No. PCT/US2015/048470 dated Dec. 10, 2015.
International Search Report and Written Opinion for International Application No. PCT/US2015/048484 dated Dec. 4, 2015.
International Search Report and Written Opinion for International Application No. PCT/US2015/048515 dated Dec. 8, 2015.
International Search Report and Written Opinion for International Application No. PCT/US17/63000 dated Apr. 9, 2018.
Blanco et al., Interventional and intraoperative MRI at low field scanner—a review. European Journal of Radiology, Elsevier Science. 2005;56(2):130-42.
Blumich et al., NMR at low magnetic fields. Chemical Physics Letters. 2009;477(4-6):231-40.
Danieli et al., Mobile sensor for high resolution NMR spectroscopy and imaging. Journal of Magnetic Resonance, Academic Press. 2009;198(1):80-7.
Issadore et al., Miniature magnetic resonance system for point-of-care diagnostics. Lab on a Chip. 2011;11(13):2282-7.
Mair et al., 3He Lung Imaging in an Open Access, Very-Low-Field Human MRI System. Magnetic Resonance in Medicine as a Communication. Dec. 16, 2004. 19 pages.
Ruset et al., A System for Open-Access 3He Human Lung Imaging at Very Low Field. Concepts Magn Reson Part B Magn Reson Eng. 2006;29(4):210-21. doi:10.1002/cmr.b.20075. [Author Manuscript] 22 pages.
Tsai et al., An open-access, very-low-field MRI system for posture-dependent 3He human lung imaging. J Magn Reson. Aug. 2008;193(2):274-285. doi:10.1016/j.jmr.2008.05.016.

* cited by examiner

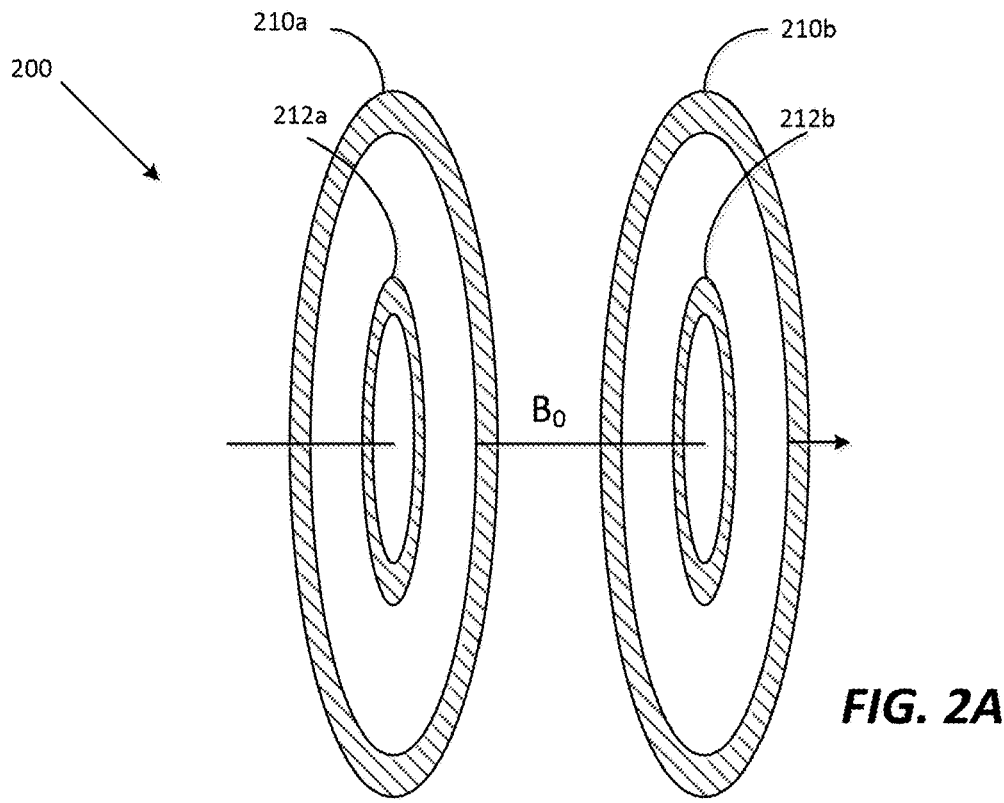
*FIG. 2A*
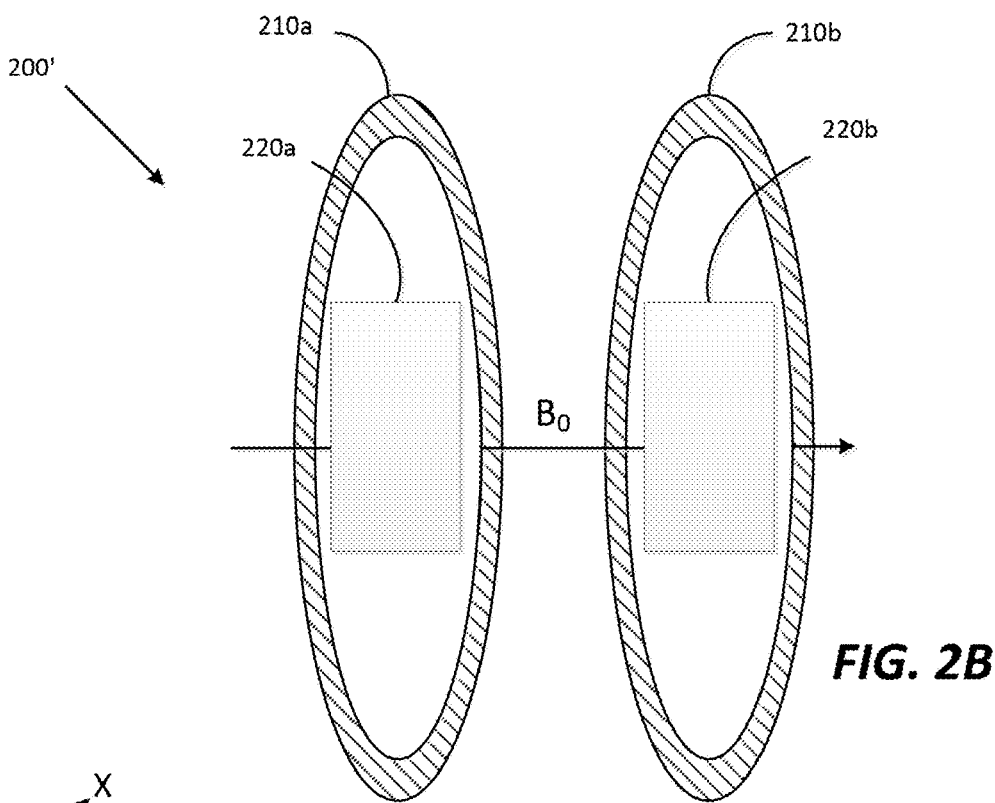
*FIG. 2B*
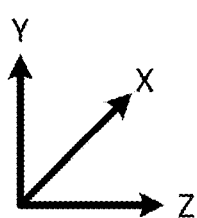

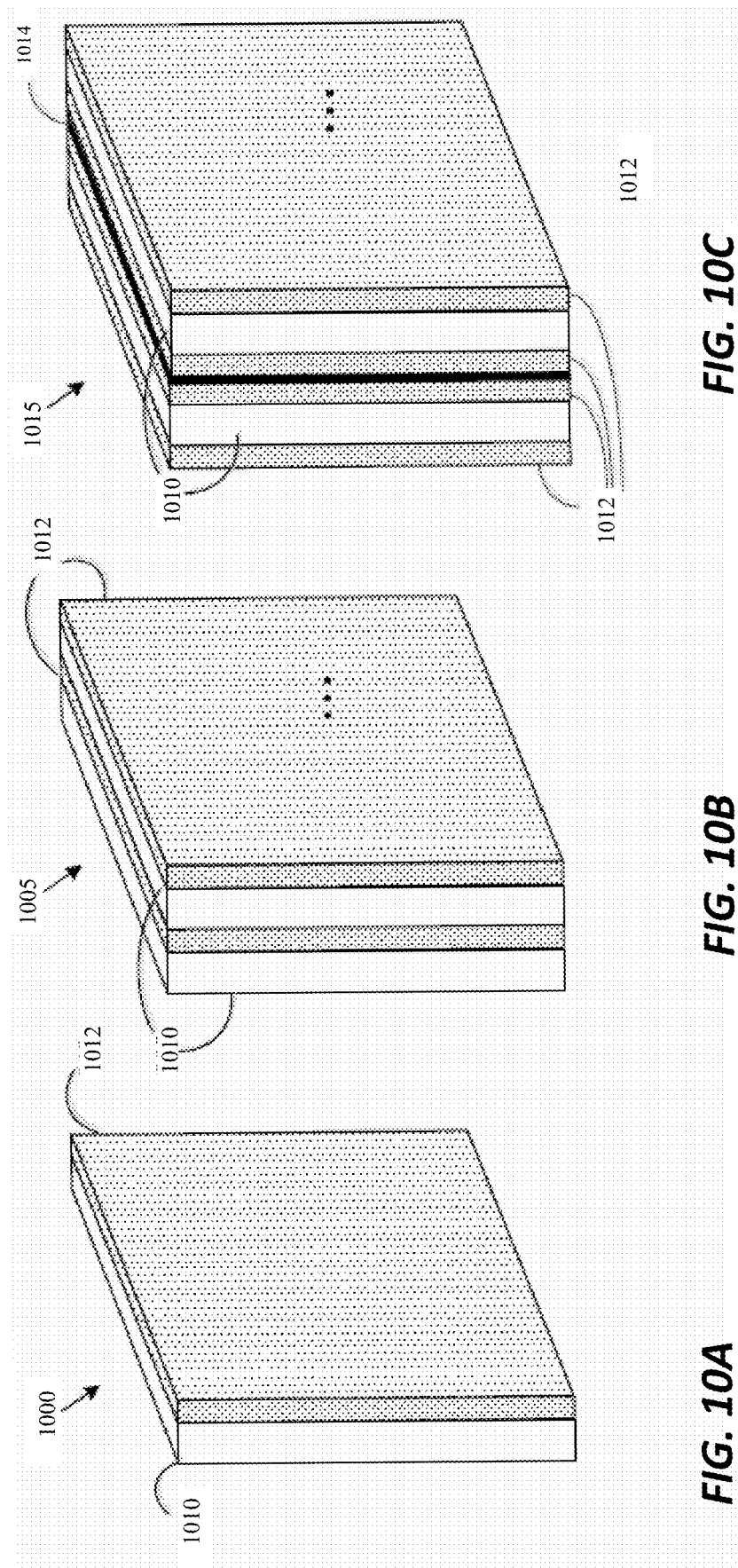

LOW FIELD MAGNETIC RESONANCE METHODS AND APPARATUS

CROSS-REFERENCE TO RELATED APPLICATIONS

This application claims priority under 35 U.S.C. § 119(e) to U.S. Provisional Patent Application Ser. No. 62/078,383, filed Nov. 11, 2014 and entitled "Low Field Magnetic Resonance Methods and Apparatus," which is herein incorporated by reference in its entirety.

BACKGROUND

Magnetic resonance imaging (MRI) provides an important imaging modality for numerous applications and is widely utilized in clinical and research settings to produce images of the inside of the human body. Generally, MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

MRI provides an attractive modality for biological exploration due to the ability to non-invasively produce information on biological structure with relatively high resolution and contrast without the safety concerns of other modalities (e.g., without needing to expose the subject to ionizing radiation, e.g., x-rays, or introducing radioactive material to the body). Additionally, MRI is particularly well suited to provide soft tissue contrast, which can be exploited to image subject matter that other imaging modalities are incapable of satisfactorily imaging. Moreover, MR techniques are capable of capturing information about structures and/or biological processes that other modalities are incapable of acquiring. However, there are a number of drawbacks to MRI that, for a given imaging application, may involve the relatively high cost of the equipment, limited availability and/or difficulty in gaining access to clinical MRI scanners and/or the length of the image acquisition process.

The trend in clinical MRI has been to increase the field strength of MRI scanners to improve one or more of scan time, resolution, and contrast, which, in turn, continues to drive up costs. The vast majority of installed MRI scanners operate at 1.5 or 3 tesla (T), which refers to the field strength of the main magnetic field B0. A rough cost estimate for a clinical MRI scanner is on the order of one million dollars per tesla, which does not factor in the substantial operation, service, and maintenance costs involved in operating such MRI scanners.

Additionally, conventional high-field MRI systems typically require large superconducting magnets and associated electronics to generate a strong uniform static magnetic field (B0) in which an object (e.g., a patient) is placed. The size of such systems is considerable with a typical MRI installment including multiple rooms for the magnet, electronics, thermal management system, and control console areas. The size and expense of MRI systems generally limits their usage to facilities, such as hospitals and academic research centers, which have sufficient space and resources to purchase and maintain them. The high cost and substantial space requirements of high-field MRI systems results in limited availability of MRI scanners. As such, there are frequently clinical situations in which an MRI scan would be beneficial, but due to one or more of the limitations discussed above, is not practical or is impossible, as discussed in further detail below.

For the reasons described above, MRI is also attractive for use in conjunction with other modalities to facilitate a variety of different types of biological investigations, both for diagnostic and therapeutic purposes and for functional applications as well, as discussed in further detail below. For example, MRI may be used in conjunction with electroencephalography (EEG) to acquire structural brain data from which a patient-specific head model may be created to facilitate accurate source localization in EEG measurements. As another example, MRI has been used as an imaging tool to assist and/or guide surgeons such as in performing tissue ablation with focused ultrasound.

However, the drawbacks of high field MRI discussed above have a similar impact on combined modality procedures and is frequently a gating factor in the ability to perform them. In particular, the high cost and limited availability prevents these procedures from being performed except in exceptional circumstances. For example, when an MR image of a patient is required to generate an accurate head model for performing EEG source localization, the limited availability of MRI scanners restricts EEG-based functional neuroimaging to environments that include a high-field MRI system and to the rare circumstances where the substantial costs are justified. Additionally, high-field MRI equipment presents an obstacle to performing MRI-assisted surgical procedures. For example, high-field MRI scanners typically include a long cylindrical bore in which patients are inserted to perform imaging, which severely restricts access to the patient. Moreover, the high-field strength of clinical MRI systems prevents the use of any metal tools or instruments from being utilized in the vicinity of the MRI magnet.

SUMMARY

The inventors have recognized that the low field strengths and/or system configurations made possible by low field strengths of low-field MR facilitates its use with other clinical techniques, such as electrophysiological devices configured to obtain electrophysiological data. Obtained MR and electrophysiological data may be utilized in conjunction to improve diagnostic, therapeutic, functional and/or control applications, examples of which are described in further detail below.

Some embodiments include a system comprising a low-field magnetic resonance (MR) device, at least one electrophysiological device, and at least one controller configured to operate the low-field MR device to obtain MR data and to operate the at least one electrophysiological device to obtain electrophysiological data.

Some embodiments include a method of operating a system comprising a low-field magnetic resonance (MR) device and at least one electrophysiological device, the method comprising, while a patient is positioned within a field of view of the low-field MR device, operating the low-field magnetic resonance device to obtain MR data, and operating the at one electrophysiological device to obtain electrophysiological data.

Some embodiments include at least one computer readable medium having instruction encoded thereon that, when executed by at least one processor, cause a method of operating a system comprising a low-field magnetic resonance (MR) device and at least one electrophysiological device to be performed, the method comprising, while a patient is positioned within a field of view of the low-field magnetic resonance device, causing operation of the low-field MR device to obtain MR data, and causing operation of the at one electrophysiological device to obtain electrophysiological data.

The inventors have recognized that the low field strengths and/or system configurations made possible by low field strengths of low-field MR facilitates its use with therapeutic techniques to guide one or more therapies.

Some embodiments comprise a system comprising a low-field magnetic resonance imaging device configured to obtain magnetic resonance (MR) data when operated with a patient within a field of view of the low-field magnetic resonance device, at least one controller configured to operate the low-field magnetic resonance device to obtain the MR data and configured to generate at least one MR image from the MR data, and at least one therapeutic device configured to deliver therapy to the patient within the field of view of the low-field magnetic resonance device, wherein the therapy is guided, at least in part, using the at least one MR image.

Some embodiments include a method of utilizing a low-field magnetic resonance imaging (MRI) device to assist in therapy, the method comprising, while a patient is located within a field of view of the low-field MRI device, operating the low-field MRI device to obtain MR data, generating at least one MR image from the MR data, and performing at least one therapeutic technique guided, at least in part, using the at least one MR image.

BRIEF DESCRIPTION OF THE DRAWINGS

Various aspects and embodiments of the disclosed technology will be described with reference to the following figures. It should be appreciated that the figures are not necessarily drawn to scale.

FIGS. 2A and 2B illustrate a bi-planar magnet configuration, in accordance with some embodiments;

FIGS. 10A-10C are schematic illustrations of single-layer and a multi-layer laminate techniques for producing a laminate panel, in accordance with some embodiments.

DETAILED DESCRIPTION

Figure 1:
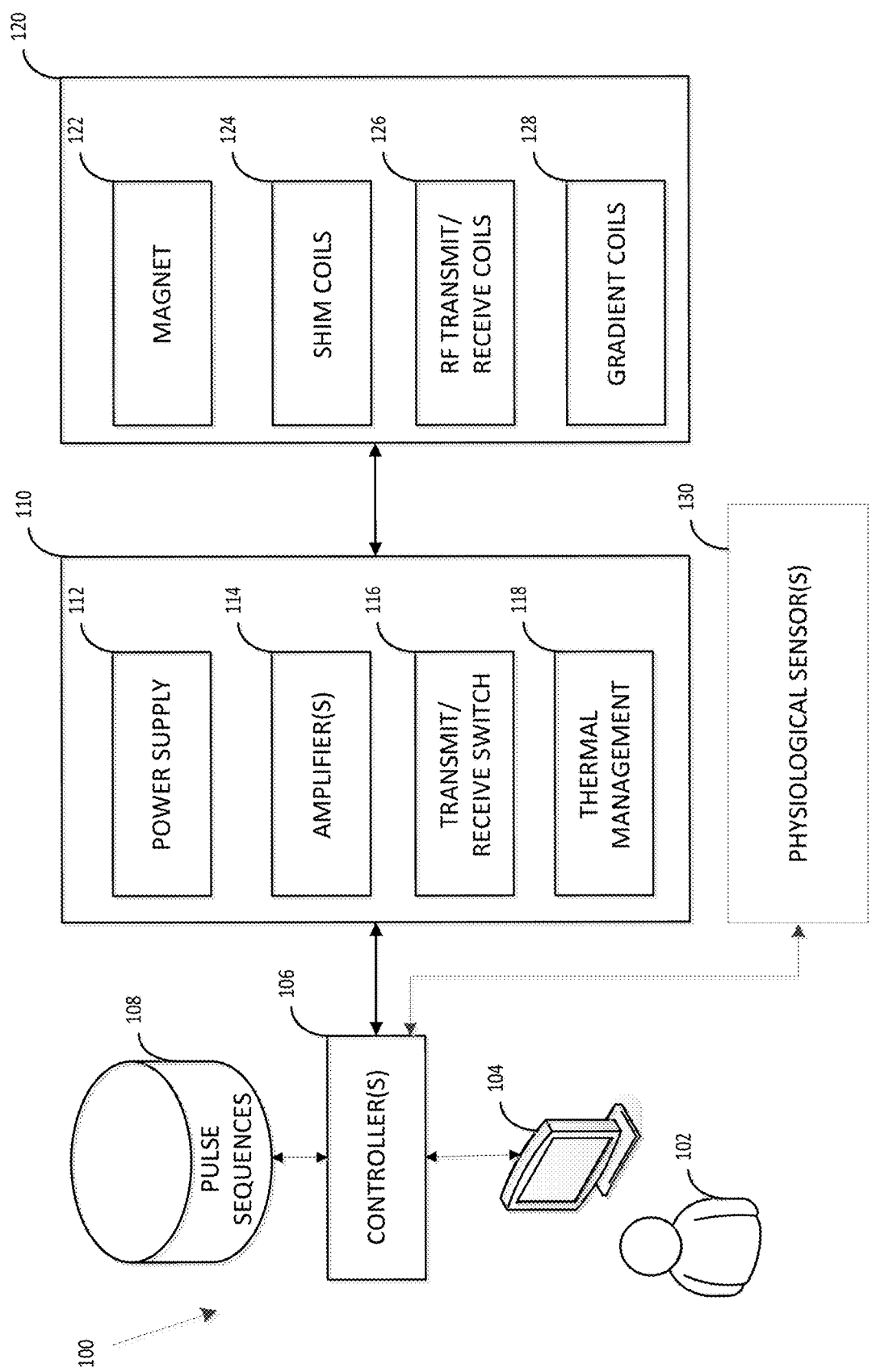
FIG. 1 illustrates a low-field MRI system including one or more electrophysiological sensors, in accordance with some embodiments.

As discussed above, in addition to being a valuable stand-alone imaging modality, MRI has the possibility of being utilized in conjunction with other modalities and/or techniques to produce valuable new tools for diagnostic, therapeutic, functional or research purposes. However, the limitations of high-field MRI severely restricts the ability of MRI to be used in conjunction with other modalities/techniques in many circumstances, if it can be utilized at all. The inventors have recognized that low-field MRI may be utilized so as to make combined modality solutions a reality that can be widely deployed with high availability, and that can be employed in circumstances where high-field MRI simply cannot. As used herein, "high-field" refers generally to MRI systems presently in use in a clinical setting and, more particularly, to MRI systems operating with a main magnetic field (i.e., a B0 field) at or above 1.5 T, though clinical systems operating between 0.5 T and 1.5 T are typically also considered "high-field." By contrast, "low-field" refers generally to MRI systems operating with a B0 field of less than or equal to approximately 0.2 T.

The general trend in medical imaging has been to produce MRI scanners with increasingly greater field strengths, with the vast majority of clinical MRI scanners operating at 1.5 T or 3 T, with higher field strengths of 7 T and 9 T used in research settings. The appeal of high-field MRI systems include improved resolution and/or reduced scan times compared to lower field systems, motivating the push for higher and higher field strengths for clinical and medical MRI applications. However, as discussed above, increasing the field strength of MRI systems yields increasingly more expensive and complex MRI scanners, not only limiting availability and preventing their use as a general purpose and/or generally available imaging solution, but putting them further out of reach for use with other modalities and/or in connection with other clinical procedures, as discussed in further detail below.

The inventors have appreciated that low field MRI can be combined with one or more electrophysiological techniques, such as EEG, to produce a functional neuroimaging system that is affordable, can be widely deployed and can be manufactured with a relatively small footprint for flexible deployment and, in some embodiments, portability. According to some embodiments, such a functional neuroimaging system may be used for diagnosing and monitoring neurophysiological disease, and has remarkable potential to revolutionize the way that medical providers treat brain injury. From diagnosing epilepsy and stroke in developing countries to quickly evaluating brain trauma of accident victims to identifying concussion symptoms of athletes in contact sports, functional neuroimaging systems designed in accordance with the techniques described herein may, in some embodiments, allow for the rapid identification of brain trauma in environments where traditional high-field MRI is not available.

According to some embodiments, an electrophysiological measurement system, such as EEG, is combined with a low-field MRI system to provide spatiotemporal functional neuroimaging data that can be used as a diagnostic (e.g., to diagnose and monitor any of a large number of neurological disease states), for therapeutic purpose (e.g., to monitor brain activity during therapeutic procedures such as transcranial magnetic stimulation), or for functional application such as using the neuroimaging data in control applications (e.g., thought control for prosthetics, mind operation of systems and apparatus, gaming, etc.). It should be appreciated that low-field MRI may be combined with any electrophysiological technique and is not limited to EEG or the brain, and may include combinations with electrocardiography (ECG), electromyography (EMG), electrooculography (EOG), etc., to obtain spatiotemporal data of a wide array of physiological phenomena, as the aspects are not limited in this respect.

MR data and electrophysiological data may be combined in any of a variety of ways, including overlaying electrophysiological data on MRI data, displaying simultaneously acquired MRI data and electrophysiological data, or otherwise utilizing the MR data and electrophysiological data in conjunction. According to some embodiments, the electrophysiological data is transformed to one or more electrophysiological images (e.g., one or more EEG images), which can be utilized in conjunction with MRI data, for example, as an overlay, as supplementary information, to guide further acquisition of MR or electrophysiological data and/or to modify parameter(s) or characteristic(s) of the MR acquisition process, the electrophysiological acquisition process or both.

The inventors have further appreciated that low-field MRI may be utilized to assist surgeons in performing surgeries for which it is useful or, in some cases, critical to provide image data to guide or otherwise facilitate the surgical procedure. As discussed above, closed bore configurations of high field MRI (e.g., solenoid magnet configurations) restrict access to the patient and prevent high field MRI from being conveniently employed in many surgical procedures, if it can be employed at all. Low-field MRI systems can be constructed according to generally "open" configurations that greatly improve access to the patient, allowing for the potential of low-field MRI to be employed in a vastly increased number of surgical procedures. Additionally, the inventors have recognized that low-field strengths utilized in low-field MRI systems relax the strict limitations on the materials that can be located near the magnetics components of the system, thus facilitating the use of an increased array of tools and instruments that can be utilized during the procedure. For example, according to some embodiments, low-field MRI is utilized in combination with focused ultrasound to assist a surgeon in performing a tissue ablation procedure.

Following below are more detailed descriptions of various concepts related to, and embodiments of, methods and apparatus for combining low-field MRI with one or more other modalities and/or techniques. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

Low-field MR has been explored in limited contexts for non-imaging research purposes and narrow and specific contrast-enhanced imaging applications, but is conventionally regarded as being unsuitable for producing clinically-useful images. For example, the resolution, contrast, and/or image acquisition time is generally not regarded as being suitable for clinical purposes such as, but not limited to, tissue differentiation, blood flow or perfusion imaging, diffusion-weighted (DW) or diffusion tensor (DT) imaging, functional MRI (fMRI), etc. The inventors have developed techniques for producing improved quality, portable and/or lower-cost low-field MRI systems that can improve the wide-scale deployability of MRI technology in a variety of environments beyond the large MRI installments at hospitals, designated MRI facilities and research institutions. The inventors have recognized that low-field MRI can be utilized with other modalities, such as EEG, to facilitate clinical diagnostic, therapeutic and functional activities previously unavailable or difficult to implement.

FIG. 1 is a block diagram of exemplary components of a MRI system 100. In the illustrative example of FIG. 1, MRI system 100 comprises workstation 104, controller 106, pulse sequences store 108, power management system 110, magnetics components 120, and electrophysiological sensor(s) 130. It should be appreciated that system 100 is illustrative and that a MRI system may have one or more other components of any suitable type in addition to or instead of the components illustrated in FIG. 1.

As illustrated in FIG. 1, magnetics components 120 comprises $B_0$ magnet 122, shim coils 124, RF transmit and receive coils 126, and gradient coils 128. $B_0$ magnet 122 may be used to generate, at least in part, the main magnetic field $B_0$. $B_0$ magnet 122 may be any suitable type of magnet that can generate a main magnetic field (e.g., a low-field strength of approximately 0.2 T or less), and may include one or more $B_0$ coils, correction coils, etc. Shim coils 124 may be used to contribute magnetic field(s) to improve the homogeneity of the $B_0$ field generated by magnet 122. Gradient coils 128 may be arranged to provide gradient fields and, for example, may be arranged to generate gradients in the magnetic field in three substantially orthogonal directions (X, Y, Z) to localize where MR signals are induced.

RF transmit and receive coils 126 may comprise one or more transmit coils that may be used to generate RF pulses to induce a magnetic field $B_1$. The transmit/receive coil(s) may be configured to generate any suitable type of RF pulses configured to excite an MR response in a subject and detect the resulting MR signals emitted. RF transmit and receive coils 126 may include one or multiple transmit coils and one or multiple receive coils. The configuration of the transmit/receive coils varies with implementation and may include a single coil for both transmitting and receiving, separate coils for transmitting and receiving, multiple coils for transmitting and/or receiving, or any combination to achieve single channel or parallel MRI systems. Thus, the transmit/receive magnetics component is often referred to as Tx/Rx or Tx/Rx coils to generically refer to the various configurations for the transmit and receive component of an MRI system. Each of magnetics components 120 may be constructed in any suitable way to, together, produce a low-field main magnetic field B0 and to stimulate and detect MR signals.

Power management system 110 includes electronics to provide operating power to one or more components of the low-field MRI system 100. For example, as discussed in more detail below, power management system 110 may include one or more power supplies, gradient power amplifiers, transmit coil amplifiers, and/or any other suitable power electronics needed to provide suitable operating power to energize and operate components of the low-field MRI system 100.

As illustrated in FIG. 1, power management system 110 comprises power supply 112, amplifier(s) 114, transmit/receive switch 116, and thermal management components 118. Power supply 112 includes electronics to provide operating power to magnetics components 120 of the low-field MRI system 100. For example, power supply 112 may include electronics to provide operating power to one or more $B_0$ coils (e.g., $B_0$ magnet 122) to produce the main magnetic field for the low-field MRI system. In some embodiments, power supply 112 is a unipolar, continuous wave (CW) power supply, however, any suitable power supply may be used. Transmit/receive switch 116 may be used to select whether RF transmit coils or RF receive coils are being operated.

Amplifier(s) 114 may include one or more RF receive (Rx) pre-amplifiers that amplify MR signals detected by one or more RF receive coils (e.g., coils 124), one or more RF transmit (Tx) amplifiers configured to provide power to one or more RF transmit coils (e.g., coils 126), one or more gradient power amplifiers configured to provide power to one or more gradient coils (e.g., gradient coils 128), shim amplifiers configured to provide power to one or more shim coils (e.g., shim coils 124).

Thermal management components 118 provide cooling for components of low-field MRI system 100 and may be configured to do so by facilitating the transfer of thermal energy generated by one or more components of the low-field MRI system 100 away from those components. Thermal management components 118 may include, without limitation, components to perform water-based or air-based cooling, which may be integrated with or arranged in close proximity to MRI components that generate heat including, but not limited to, $B_0$ coils, gradient coils, shim coils, and/or transmit/receive coils. Thermal management components 118 may include any suitable heat transfer medium including, but not limited to, air and water, to transfer heat away from components of the low-field MRI system 100.

As illustrated in FIG. 1, low-field MRI system 100 includes controller 106 (sometimes referred to as a console in the MRI context) configured to send instructions to and receive information from power management system 110. Controller 106 may be configured to implement one or more pulse sequences, which are used to determine the instructions sent to power management system 110 to operate the magnetics components 120 in a desired sequence, for example, by operating the transmit coil(s) and/or the gradient coils in the particular sequence defined by the pulse sequence. A pulse sequence generally describes the order and timing in which transmit/receive coils and gradient coils operate to prepare the magnetization of the subject and acquire resulting MR data. For example, a pulse sequence may indicate an order of transmit pulses, gradient pulses, and acquisition times during which the receive coils acquire MR data.

Controller 106 may be configured to control power management system 110 to operate the magnetics components 120 in accordance with a balance steady-state free precession (bSSFP) pulse sequence, a low-field gradient echo pulse sequence, a low-field spin echo pulse sequence, a low-field inversion recovery pulse sequence, arterial spin labeling, diffusion weighted imaging (DWI), and/or any other suitable pulse sequence. Pulse sequences for low-field MRI may be applied for different contrast types such as T1-weighted and T2-weighted imaging, diffusion-weighted imaging, arterial spin labeling (perfusion imaging), Overhauser imaging, etc., each of which have a particular set of considerations in the low-field context. Controller 106 may be implemented as hardware, software, or any suitable combination of hardware and software, as aspects of the disclosure provided herein are not limited in this respect.

In some embodiments, controller 106 may be configured to implement a pulse sequence by obtaining information about the pulse sequence from pulse sequences repository 108, which stores information for each of one or more pulse sequences. Information stored by pulse sequences repository 108 for a particular pulse sequence may be any suitable information that allows controller 106 to implement the particular pulse sequence. For example, information stored in pulse sequences repository 108 for a pulse sequence may include one or more parameters for operating magnetics components 120 in accordance with the pulse sequence (e.g., parameters for operating the RF transmit and receive coils 126, parameters for operating gradient coils 128, etc.), one or more parameters for operating power management system 110 in accordance with the pulse sequence, one or more programs comprising instructions that, when executed by controller 106, cause controller 106 to control system 100 to operate in accordance with the pulse sequence, and/or any other suitable information. Information stored in pulse sequences repository 108 may be stored on one or more non-transitory storage media.

As illustrated in FIG. 1, controller 106 also interacts with computing device 104 programmed to process received MR data. For example, computing device 104 may process received MR data to generate one or more MR images using any suitable image reconstruction process(es). Controller 106 may provide information about one or more pulse sequences to computing device 104 for the processing of data by the computing device. For example, controller 106 may provide information about one or more pulse sequences to computing device 104 and the computing device may perform an image reconstruction process based, at least in part, on the provided information.

Computing device 104 may be any electronic device, and typically includes one or more processors configured (e.g., programmed) to process acquired MR data and generate one or more images of the subject being imaged. In some embodiments, computing device 104 may be a fixed electronic device such as a desktop computer, a server, a rack-mounted computer, or any other suitable fixed electronic device that may be configured to process MR data and generate one or more images of the subject being imaged. Alternatively, computing device 104 may be a portable device such as a smart phone, a personal digital assistant, a laptop computer, a tablet computer, or any other portable device that may be configured to process MR data and generate one or images of the subject being imaged.

Controller 106 is further configured to send instructions to and receive information from physiological sensor(s) 130. For example, physiological sensor(s) 130 may comprise a plurality of electrodes and associated electronics that form, at least in part, an EEG device capable of obtaining EEG data from a patient. Alternatively, or in addition to, physiological sensor(s) 130 may include electrophysiological sensors for performing electromyography (EMG), electrooculography (EOG), electrocardiography (ECG), or the like. In some embodiments, physiological sensor(s) 130 include optical imaging sensors. In yet other embodiments, physiological sensor(s) 130 includes one or more ultrasound transducers to facilitate ultrasound imaging. Other types of physiological sensor(s) may also be used, as the aspects are not limited in this respect. Controller 106 may be configured to send/receive information to any one or combination of physiological sensors 130 that are provided to operate in conjunction with the low-field MRI system, examples of which are described in further detail below.

It should be appreciated that controller 106 may be a single integrated controller or may comprise separate controllers to perform functions of system 100. In some embodiments, computing device 104 may comprise multiple computing devices of any suitable type, as the aspects are not limited in this respect. A user 102 may interact with computing device 104 (e.g., a workstation) to control aspects of the low-field MR system 100 (e.g., program system 100 to operate in accordance with a particular pulse sequence, adjust one or more parameters of the system 100, operate physiological sensor(s), etc.) and/or view images obtained by the low-field MR system 100. According to some embodiments, computing device 104 and controller 106 form a single controller, while in other embodiments, computing device 104 and controller 106 each comprise one or more controllers. It should be appreciated that the functionality performed by computing device 104 and controller 106 may be distributed in any way over any combination of one or more controllers, as the aspects are not limited for use with any particular implementation or architecture. Controller 106 and computing device 104 typically comprise one or more processors capable of executing instructions embodied in computer code, such as software programs, firmware instructions, etc. to perform one or more functions in connection with the operation of system 100.

FIGS. 2A and 2B illustrate bi-planar magnetic configurations that may be used in a low-field MRI system suitable for use with techniques described herein. FIG. 2A schematically illustrates a bi-planar magnet configured to produce, at least in part, a portion of a $B_0$ field suitable for low-field MRI. Bi-planar magnet 200 comprises two outer coils 210a and 210b and two inner coils 212a and 212b. When appropriate current is applied to the coils, a magnetic field is generated in the direction indicated by the arrow to produce a $B_0$ field having a field of view between the coils that, when designed and constructed appropriately, may be suitable for low-field MRI. The term "coil" is used herein to refer to any conductor or combination of conductors of any geometry having at least one "turn" that conducts current to produce a magnetic field, thereby forming an electromagnet.

It should be appreciated that the bi-planar geometry illustrated in FIG. 2A is generally unsuitable for high-field MRI due to the difficulty in obtaining a $B_0$ field of sufficient homogeneity at high-field strengths. High-field MRI systems typically utilize solenoid geometries (and superconducting wires) to achieve the high field strengths of sufficient homogeneity for high-field MRI. The bi-planar $B_0$ magnet illustrated in FIG. 2A provides a generally open geometry, facilitating its use in many circumstances where high-field MRI systems cannot. For example, generally open geometries provide improved access to patients to facilitate combining low-field MRI with one or more other modalities, techniques and/or surgical procedures, including those that are difficult or impossible using conventional high-field closed bore configurations. Also, open geometries can be used with patients who suffer from claustrophobia and may refuse to be imaged with conventional high-field solenoid coil geometries. Furthermore, the bi-planar design may facilitate use with larger patients as a result of its open design and, in some instances, a generally larger field of view possible at low-field strengths and homogeneity requirements. Moreover, the generally open design facilitates access to the patient being imaged and may improve the ability to position a patient within the field of view, for example, an unconscious, sedated or anesthetized patient.

As discussed above, the inventors have further recognized that open geometries allow access to the patient, facilitating the use of MRI during other clinical procedures such as during a surgery or other procedures where some measure of access to the patient is desired or required. In general, combining MRI with other modalities and/or clinical procedures is not possible using conventional MRI due to the closed configuration and/or the high field-strengths involved, as discussed in further detail below. The bi-planar geometry in FIG. 2A is merely exemplary, and other configurations may be used. For example, according to some embodiments, a "one-sided" geometry is used wherein the $B_0$ magnet essentially consists of single side, in contrast to the pair of opposing sides in the bi-planar geometry illustrated. One-sided geometries provide substantially full access to the patient being imaged.

FIG. 2B illustrates a hybrid bi-planar magnet using laminate techniques to fabricate a $B_0$ magnet or portion thereof and/or to fabricate one or more other magnetics components for use in low-field MRI. For example, in the exemplary bi-planar magnet 200' illustrated in FIG. 2B, laminate panels 220a and 220b replace inner coils 212a and 212b to produce a hybrid magnet. Laminate panels 220a and 220b may include any number of laminate layers having fabricated thereon one or more $B_0$ coils, gradient coils, correction coils and/or shim coils, etc. or portions thereof to facilitate production of the magnetic fields used in low-field MRI. Suitable hybrid magnets using laminate techniques are described in U.S. patent application Ser. No. 14/845,652 ('652 application), filed Sep. 4, 2015 and titled "Low Field Magnetic Resonance Imaging Methods and Apparatus," which is herein incorporated by reference in its entirety. In other embodiments, laminate techniques can be used to implement the $B_0$ magnet in its entirety (e.g., replacing coils 210a and 210b).

Exemplary laminate panels 220a and 220b may, additionally or alternatively, have fabricated thereon one or more gradient coils, or portions thereof, to encode the spatial location of received MR signals as a function of frequency or phase. According to some embodiments, a laminate panel comprises at least one conductive layer patterned to form one or more gradient coils, or a portion of one or more gradient coils, capable of producing or contributing to magnetic fields suitable for providing spatial encoding of detected MR signals when operated in a low-field MRI system. For example, laminate panel 220a and/or laminate panel 220b may comprise a first gradient coil configured to selectively vary the $B_0$ field in a first (X) direction to perform frequency encoding in that direction, a second gradient coil configured to selectively vary the $B_0$ field in a second (Y) direction substantially orthogonal to the first direction to perform phase encoding, and/or a third gradient coil configured to selectively vary the $B_0$ field in a third (Z) direction substantially orthogonal to the first and second directions to enable slice selection for volumetric imaging applications.

Exemplary laminate panels 220a and 220b may, additionally or alternatively, include additional magnetics components such as one or more correction or shim coils arranged to generate magnetic fields in support of the system to, for example, increase the strength and/or improve the homogeneity of the $B_0$ field, counteract deleterious field effects such as those created by operation of the gradient coils, loading effects of the object being imaged, other equipment in proximity or being used in conjunction, or to otherwise support the magnetics of the low field MRI system. The bi-planar magnet illustrated in FIGS. 2A and 2B, may be produced using conventional coils, laminate techniques, or a combination of both, and may be used to provide magnetics components for a low-field MRI system, as discussed in further detail below.

FIG. 10A schematically illustrates a laminate panel 1000 that includes a single non-conductive layer 1010 and a single conductive layer 1012 formed on the non-conductive layer.

The non-conductive layer 1010 (also referred to herein as a substrate) may be formed from any suitable material. For example, substrate 1010 may be formed from any one or combination of suitable core materials, composites, adhesives and/or laminates may be utilized to form non-conductive layers and facilitate producing a laminate panel, including, but not limited to, FR4, ceramic, plastic, glass, polymide, epoxy, pre-impregnated composite fibers (pre-preg), multifunctional epoxy laminates such as 92 ML, or any other material(s) or combinations thereof having suitable properties. Substrate 1010 may be a single layer or constructed of multiple layers of non-conductive material, each layer of which may be made from a same or different non-conductive material. Layering the substrate may allow for construction of a substrate that utilizes beneficial properties of different materials. Substrate 1010 may be constructed to any desired dimensions, having length, width and thickness suitable for a given design.

Likewise, conductive layer 1012 may be formed from any suitable conducting material. For example, conductive layer 1012 may be a thin or thick film of copper or other suitable conductive material, a thick or extremely thick conductive layer (e.g., "extreme copper"), conductive plate, or any other type of conductive layer capable of being formed as a laminate on non-conductive substrate 1010 by any suitable technique or process (e.g., via dip coating, electroplating, printing, molding, bonding, vacuum impregnating, pressing, dry adhesive, or any other suitable technique(s)). According to some embodiments, aluminum may be used as a conductor to take advantage of associated cost and weight reductions, as discussed in further detail below.

To produce desired "circuitry," conductive layer(s) 1012 may be patterned to form electrical conductors for desired portions of one or more magnetic components of a low-field MRI apparatus using any one or combination of various subtractive, additive and/or semi-additive processes. Subtractive processes selectively remove the conductive material (e.g., copper) from the conductive layer leaving a desired conductive pattern providing a desired conducting circuit or portion of a circuit using, for example, any of various lithographic processes including, but not limited to, chemical etching, photoengraving, etc. Such processes are performed by providing a resist material in the desired pattern (often referred to as a mask) and introducing the conductive layer to the corresponding etchant to remove the conductive material in locations not treated with the resist material. Another subtractive process involves milling away unwanted portions of the conductive layer leaving the desired conductive pattern. The subtractive processes described herein and/or any other suitable process may be used alone or in any combination to fabricate the desired conductive pattern.

Additive processes may involve electroplating the desired conductive pattern on the substrate or "printing" the pattern using a conductive ink. For example, electroplating may involve exposing photosensitive film masked in a desired pattern. The exposed pattern may then be introduced to a chemical bath to allow the pattern to be capable of metal ion bonding and then plated with a conductor (e.g., with copper) that bonds with the pattern sensitized in the chemical bath to form the desired conductive pattern. Additive processes have the advantage that less conductive material is needed to form the desired conductive pattern than subtractive techniques. Other processes combine both subtractive and additive techniques to form the desired conductive pattern.

According to some embodiments, one or more magnetic components fabricated using laminate techniques may require conductive layers to be fabricated at relatively large thicknesses, often referred to as "heavy copper," (e.g., 5 oz/ft$^2$-19 oz/ft$^2$) or "extreme copper," (e.g., 20 oz/ft$^2$-200 oz/ft$^2$), though the techniques apply regardless of the choice of conductor material. Examples of suitable techniques for patterning heavy or extreme copper include, but are not limited to, any one or combination of cupric chloride etch, ferric chloride etch, mechanical milling, plasma etch, laser etch, electro-discharge-machining (EDM), plating up, etc. It should be appreciated that any single technique or combination of techniques described herein may be utilized, or any other technique suitable for patterning a conductive layer on a non-conductive substrate and/or for producing a laminate panel may be used, as aspects of forming one or more magnetic components (or portions thereof) of a low field MRI system in a laminate panel are not limited to any particular technique or combination of techniques for doing so.

FIG. 10B schematically illustrates a laminate panel 1005 that includes a plurality of non-conductive layers 1010 and a plurality of conductive layers 1012 formed between the non-conductive layers. Connections between the conductive layers 1012 may be achieved by forming holes filled with a conductive material (e.g., plated through-holes) in the intervening non-conductive layers called "vias," as described in more detail below. Although only two non-conductive layers and two conductive layers are explicitly illustrated in FIG. 10B, as indicated by the ellipses, any number of non-conductive layers and conductive layers may be used to achieve a laminate panel according to a desired design, some examples of which are described in further detail below.

Additionally, it should be appreciated that multiple conductive layers may be provided for each non-conductive layer, for example, a non-conductive layer having a conductive layer laminated to both sides. FIG. 10C illustrates a multi-layer panel formed by attaching together two laminate layers, each having a non-conductive layer 1010 with a conductive layer laminated to both sides of the respective non-conductive layer. The multi-layer laminates may be attached using one or more adhesive layers 1014. Adhesive layer(s) 1014 may be any suitable adhesive or combination of materials such as pre-preg, dry adhesive, epoxy and/or any other suitable layer or combination of layers that, when activated (e.g., via heat and/or pressure) bonds the multi-layer laminates together. It should be appreciated that any configuration of conductive and non-conductive layering, adhesives, etc., using any one or combination of lamination techniques may be used to produce a desired laminate panel.

Figure 11:
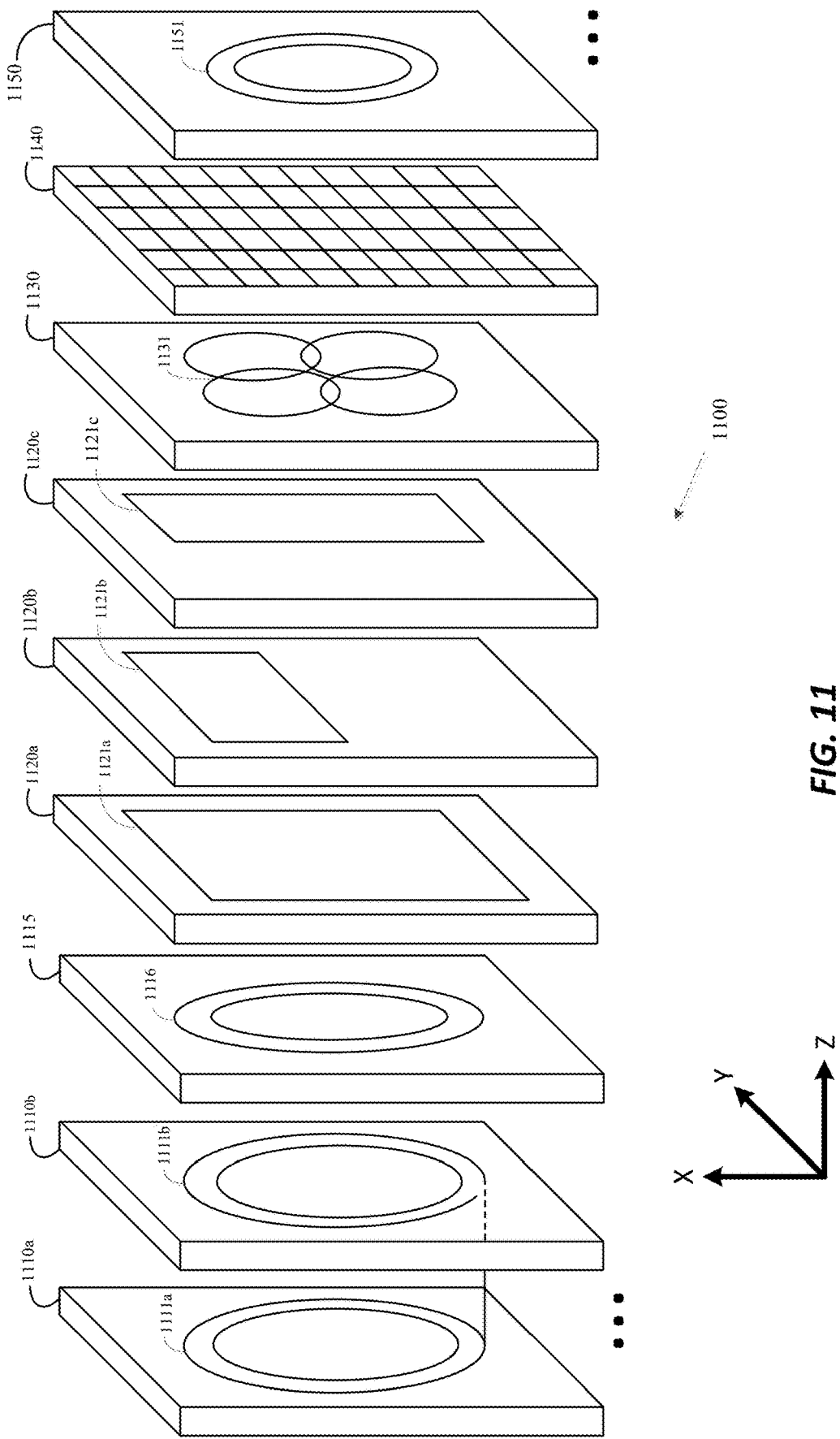
FIG. 11 shows an exploded view of example magnetic components of a low-field MRI system formed on layers of a multi-layer laminate panel, in accordance with some embodiments.

FIG. 11 illustrates a schematic view of an exemplary multi-layer laminate panel 1100 for use with a low-field MRI system, in accordance with some embodiments. It should be appreciated that laminate panel 1100 is depicted as such to illustrate some examples of components that may be fabricated via laminate techniques. However, it should be appreciated that a laminate panel need not include all of the components illustrated in FIG. 11, and any one or more of the illustrated components may be omitted as desired. That is, a laminate panel may include any one or combination of the exemplary layers illustrated in FIG. 11 to form any one or combination of components (or portions thereof) in the laminate panel. In addition, a laminate panel may include other layers not illustrated in FIG. 11 (e.g., one or more layers for thermal management, one or more interconnect layers, one or more layers having control electronics or other electronic components, etc.).

The illustrated components (or any desired subset) may be formed in one or multiple layers, and separate components may be formed on layers shared with other components, or formed on separate layers independent from other components. To simplify illustration of a multi-layer panel (and the nearly limitless combination of layers and configurations thereof), the magnetic components illustrated in FIG. 11 are shown schematically without limitation on geometry of the magnetic components, or the number of layers on which they may be fabricated. As such, the exemplary layers illustrated in FIG. 11 and described herein should be understood to represent either a single laminate layer composed of at least one non-conductive layer and at least one conductive layer, or multiple such laminate layers, each composed of one or more non-conductive layers and one or more conductive layers. Accordingly, unless otherwise specified, a layer refers to one or more laminate layers.

It should be further appreciated that the illustrations in FIG. 11 showing the various components that may be fabricated within panel 1100 are used to generically represent the respective component and are not intended to depict any particular geometry or configuration. The components illustrated in FIG. 11 may be patterned according to any desired geometry and configuration, as the techniques described herein for integrating one or more magnetic components within a laminate panel are not limited for use with any particular geometry, configuration or arrangement. Some examples of suitable geometries that may be utilized are discussed without limitation in further detail below.

As shown, exemplary laminate panel 1100 includes a plurality of $B_0$ layers (1110a, 1110b) having one or more $B_0$ coils (1111a, 1111b) formed thereon. The $B_0$ coils are configured to generate at least a portion of a $B_0$ field for the low-field MRI system when an appropriate current is applied to the coil(s). In some embodiments, each $B_0$ layer includes one or more turns of a conductive trace patterned on the conductive layer to generate a portion of a desired $B_0$ field. As shown, layer 1110a has patterned thereon a coil 1111a, which may be patterned according to any desired geometry. For example, coil 1111a may be patterned according to a generally circular geometry have one or more turns of conductive traces. Coil 1111a may be electrically connected to coil 1111b patterned on layer 1110b (e.g., by a via between the layers), which also may be of any desired geometry (e.g., a generally circular coil having one or more turn of a conductor).

It should be appreciated that any suitable number of layers having $B_0$ coils formed thereon may be interposed between and electrically connected to layers 1110a and 1110b (e.g., 1, 10, 20, 50 or more layers, etc), each having one or more respective coils formed thereon that, when energized with a suitable current, provides at least a portion of a $B_0$ field configured for use in low-field MRI. It should be appreciated that each layer may have a single coil or multiple coils, and each coil may be patterned to have any number of turns formed thereon to achieve the magnetic and/or electric properties of a desired coil design.

The inventors have recognized and appreciated that using laminate techniques to design and manufacture MRI components enables the fabrication of $B_0$ coils having arbitrary geometries and configurations not practicable or possible using conventional techniques for manufacturing $B_0$ coils for low-field MRI systems, allowing for coil designs of virtually any geometry, configuration and/or arrangement. According to some embodiments, at least some $B_0$ layers on which one or more coils, or portions thereof, are formed may be patterned using different coil geometries than other layers to achieve a desired $B_0$ field. Some $B_0$ layers may have formed thereon one or more coils that can be independently controlled to tune the $B_0$ field for different applications and environments, or to adjust the $B_0$ field to calibrate or otherwise achieve a $B_0$ field of desired strength and/or homogeneity, as discussed in further detail below.

The selection of a particular coil geometry or combination of coil geometries and the arrangement and distribution of the coils within a laminate panel may depend, at least in part, on a desired $B_0$ field to be generated for use with low-field MRI applications. Additionally, one or more laminate layers having the same or different $B_0$ coil design may be connected by one or more vias connecting the conductive traces on the multiple layers. In some embodiments, the locations of the vias may be selected to minimize their effect on the homogeneity of the resultant $B_0$ field and/or to generally optimize one or more electrical properties of the energized coil. Non-limiting examples of $B_0$ coil designs that may be used to form, at least in part, a $B_0$ magnet for use in low-field MRI, are described in further detail below.

Because laminate techniques are capable of patterning electrical conductors with such high precision and accuracy, a $B_0$ magnet (or any portion thereof) may be fabricated in laminate panel form reliably and with high fidelity in accordance with the design specifications for a particular $B_0$ magnet to achieve a $B_0$ field of desired strength and homogeneity. Additionally, the ability to distribute one or more $B_0$ coils forming a $B_0$ magnet (or a portion thereof) over multiple layers of a laminate panel allows for optimizing the parameters of the $B_0$ magnet to generate a desired $B_0$ field in a manner not possible using conventional techniques for producing a $B_0$ magnet. Simulations may be used to select among numerous geometries, configurations and/or arrangements (e.g., the position, geometry or other properties of electrical conductors on each layer contributing the $B_0$ field may be generally optimized) to produce a desired $B_0$ field. The resulting design may then be precisely and accurately fabricated using suitable laminate techniques.

According to some embodiments, one or more laminate layers may include passive magnetic component(s), such as one or more layers patterned with magnetic materials, to facilitate the generation of a desired $B_0$ field with reduced power requirements, or to produce a higher $B_0$ field using the same power requirements as needed without the use of magnetic materials. For example, laminate panel 1100 may include one or more laminate layers 1115 patterned with ferrous, or other magnetic materials, arranged to form a magnetic component 1116 that contributes to the magnetic field generated by one or more $B_0$ coils to achieve a desired $B_0$ field. Because such magnetic materials produce or tailor a magnetic field without needing a power source to provide current to produce a magnetic field, a desired $B_0$ field may be produced with reduced power requirements. Additionally, because magnetic materials can be used to produce a higher $B_0$ field without a corresponding increase in power requirements, magnetic materials may facilitate the construction of a low-field MRI system having a higher $B_0$ field, potentially exceeding 0.2 T (e.g., between 0.2 T and 0.5 T).

Magnetic component(s) 1116 formed on one or more layers 1115 may include any one or combination of materials having relatively high magnetic permeability ($\mu$) to assist in producing or tailoring a $B_0$ field of desired field strength and/or homogeneity. Magnetic component(s) 1116 may be formed by one or more patterned layers, provided as a sheet, or other otherwise manufactured and incorporated within one or more laminate layers to produce a desired magnetic field. As discussed above, the use of passive magnetic components can reduce the power requirements needed to produce a given $B_0$ field. That is, because a portion of a desired $B_0$ can be produced passively (e.g., without requiring a power source to operate the components), the burden on the active magnetic components (e.g., the one or more a desired $B_0$ coils) can be reduced. As a result, one or more $B_0$ coils can be operated with reduced current to produce, in combination with magnetic component(s) 16, a $B_0$ field having a desired field strength and/or homogeneity. Reducing the power requirements of the active magnetic components simplifies the cost and complexity of the power electronics driving the magnetic components, results in a corresponding reduction in the thermal output of the laminate panel, and also may otherwise ease the constraints on the active magnetic components in generating a $B_0$ field of desired strength and/or homogeneity.

As discussed above, a laminate panel may further comprise at least one conductive layer patterned to form one or more gradient coils, or a portion of one or more gradient coils, capable of producing or contributing to magnetic fields suitable for providing spatial encoding of detected MR signals when operated in a low-field MRI system. In the example illustrated in FIG. 11, laminate panel 1100 includes a plurality of laminate layers (1120a, 1120b, 1120c) on which gradient coils (1121a, 1121b, 1121c) are formed. Layer(s) 1120a includes a conductive trace patterned to form all or a portion of a Z-gradient coil 1121a, layer(s) 1120b includes a conductive trace patterned to form all or a portion of a Y-gradient coil 1121b, and layer(s) 1120c includes a conductive trace patterned to form all or a portion of an X-gradient coil 1121c. As discussed above, the depiction of gradient coils 1121a, 1121b and 1121c in FIG. 11 is meant to generically represent gradient coils of any suitable geometry using any number and configuration of layers to provide the one or more desired gradient coils.

As one non-limiting example wherein gradient coils are at least partially formed in a laminate panel (e.g., laminate panel 1100), a Z-gradient coil may be formed, at least in part, in one or more layers using a generally circular geometry and an X-gradient coil and a Y-gradient coil may be formed, at least in part, in one or more layers using a generally rectangular geometry such as via one or more conductors patterned as a grid. The conductors for the gradient coils may be distributed across one or multiple layers in any combination as desired to produce integrated gradient coils, either with or without other magnetic components of a low field MRI system, and either sharing layers with other magnetic components and/or patterned on separate layers of a laminate panel.

In some embodiments of a laminate panel with both $B_0$ coils and gradient coils for thereon, at least one layer of the laminate panel may include both $B_0$ coils (or a portion thereof) and gradient coils (or a portion thereof) that may be selectively controlled to provide desired magnetic field characteristics for low-field imaging applications. In some embodiments, at least a portion of the same conductive trace on a layer of a laminate panel may function as a $B_0$ coil or as a gradient coil depending on how the coil is operated. According to some embodiments, a gradient coil may be distributed over multiple layers and according to some embodiments, multiple gradient coils (or portions thereof) may be formed in a single layer (e.g., one or more of X, Y and/or Z gradient coils), as the techniques described herein are not limited to any particular manner of distributing magnetic component(s) over multiple layers of a laminate panel or multiple laminate panels. It should be appreciated that one or more gradient coils fabricated using laminate techniques may be utilized in connection with one or more other magnetic components fabricated using laminate techniques (e.g., by integrating the one or more gradient coils in a shared or separate laminate panel), or may be utilized in connection with one or more other magnetic components fabricated using conventional techniques as part of a low field MRI system.

As also discussed above, a laminate panel may further comprise at least one conductive layer patterned to form one or more transmit and/or receive coils, or a portion of one or more transmit and/or receive coils, configured to stimulate MR response by producing a $B_1$ excitation field (transmit) and/or to receive emitted MR signals (receive) when operated in conjunction with the coils configured to produce a $B_0$ field and corresponding gradient fields. Such a laminate panel may incorporate single transmit and/or receive coils (or portions thereof) or multiple transmit and/or receive coils (or portions thereof) for performing single channel or parallel MRI. In the example illustrated in FIG. 11, laminate panel 1100 includes layer(s) 1130 on which all or a portion of a transmit/receive coil 1131 is formed.

Any suitable geometry may be used to pattern the transmit/receive coil or set of transmit/receive coils. For example, in some embodiments, a spiral-shape conductor may be patterned in one or more layers to form one or more transmit/receive coil (or portions thereof). According to some embodiments, a substantially rectangular geometry may be utilized to fabricate one or more transmit and/or receive coils using laminate techniques. According to some embodiments in which different coils are used for transmit and receive, transmit and receive coils may be formed in one or more layers using different respective geometries. In some embodiments, multiple layers and/or multiple laminate panels may be used to collectively form a transmit/receive coil and/or set of transmit/receive coils for use in a low field MRI system. It should be appreciated that one or more transmit/receive coils fabricated using laminate techniques may be utilized in connection with one or more other magnetic components fabricated using laminate techniques (e.g., by integrating the one or more other magnetic components in a shared or separate laminate panel), or may be utilized in connection with one or more other magnetic components fabricated using conventional techniques as part of a low field MRI system.

A laminate panel may further comprise at least one conductive layer patterned to form one or more electromagnetic shields arranged to prevent electromagnetic energy from the environment and/or generated from components of the MRI system from disturbing the magnetic fields generated by the MRI magnetics and/or for otherwise shielding the apparatus from electromagnetic interference. In the example illustrated in FIG. 11, laminate panel 1100 includes layer(s) 1140 used to provide electromagnetic shielding. Although only a single shielding layer is shown, it should be appreciated that any suitable number of shielding layers may be used in any different number of locations, and the patterned conductive layer(s) forming one or more shields may be formed in separate layers or formed on layers on which other components are formed (e.g., patterned in electrical isolation on unused portions of one or more laminate layers on which other magnetic components or portions of other magnetic portions are formed. Shielding layer(s) 1140 may be formed by patterning a conductor mesh in one or more layers of laminate panel 1100, though it should be appreciated that shielding may be provided using any suitable conductor pattern to form any desired geometry, which geometry may be selected based on where the respective shielding is provided and/or characteristics of the electromagnetic interference the particular shielding is employed to suppress or eliminate.

Electromagnetic shielding may be configured to provide active shielding or passive shielding, and embodiments are not limited in this respect. In some embodiments, shielding formed on multiple layers of a laminate panel are connected using one or more vias. Accordingly, at least some shielding for a low field MRI system may be integrated into one or more laminate panels in which one or more magnetic components are fabricated, either on one or more separate layers or on one or more layers on which another magnetic component (or portion thereof) is formed. Electromagnetic shielding may include static or dynamic shielding of magnetic fields, electric fields, or both.

Shim coils arranged to facilitate the production of desired magnetic fields may also be patterned on one or more layers of a laminate panel. According to some embodiments, a laminate panel may comprise at least one conductive layer patterned to form one or more shim coils, or a portion of one or more shim coils, arranged to produce or contribute to magnetic field(s) and adapted to improve the homogeneity of the $B_0$ field generated by one or more $B_0$ coils, to otherwise improve the $B_0$ field within a given field of view and/or to counteract other magnetic fields that negatively impact the $B_0$ field. In the example illustrated in FIG. 11, laminate panel 1100 includes layer(s) 1150 on which one or more shim coils 1151 (or portions thereof) are formed. For embodiments that include a laminate panel with at least one $B_0$ coil and at least one shim coil, the at least one shim coil may be formed by conductive layers shared with (but electrically isolated from) the at least one $B_0$ coil (or portions thereof) or may be formed in one or more conductive layers separate from the at least one $B_0$ coil (or portions thereof). As with the other magnetic components discussed, shim coils fabricated using laminate techniques may be utilized with other components fabricated using laminate techniques (e.g., by integrating the shim coils in a shared or separate laminate panel) or utilized with other components manufactured using conventional techniques as part of a low field MRI system.

As discussed above, multiple low-field MRI components (or portions thereof) may be formed on a single layer (i.e., a single laminate layer) of a laminate panel. That is, multiple magnetic components or portions of multiple magnetic components may be patterned on the same conductive layer of a single laminate layer. For example, the conductive layer of a single laminate layer may be patterned to form one or more $B_0$ coils (either forming or contributing to a complete $B_0$ magnet) and one or more gradient coils or portion of one or more gradient coils.

As a further example, a single laminate layer of a laminate panel may be patterned to form all or a portion of a gradient coil and all or a portion of a transmit/receive coil. The gradient coil and the transmit/receive coil (or portions thereof) may share at least some conductive elements formed on the laminate layer, or the gradient coil and the transmit/receive coil (or portions thereof) may be formed separately on the same laminate layer (e.g., electrically isolated from one another). As another example, a single laminate layer of a laminate panel may be patterned to form all or a portion of one or more $B_0$ coils and all or a portion of one or more shim coils used to tune the homogeneity of the $B_0$ field for the low-field MRI system. The shim coil(s) and the $B_0$ coil(s) (or portions thereof) may share at least some conductive elements formed on the laminate layer or the shim coil(s) and the $B_0$ coil (or portions thereof) may be formed separately on the same laminate layer (i.e., electrically isolated from one another). It should be appreciated that any combination of components (or portions thereof) may be similarly fabricated in one or more shared laminate layers as desired according to a specific design, as the aspects are not limited in this respect.

The inventors have recognized and appreciated that some conductors formed on laminate panels in accordance with some embodiments may be configured to perform multiple functions typically characteristic of functions performed by separate MRI components. By repurposing the same conductors to perform different functions and/or by sharing laminate layers of a laminate panel between multiple components or portions of multiple components, the dimensions and costs associated with manufacturing a laminate panel may be reduced.

It should be appreciated that the order of the laminate layers of laminate panel 1100 shown in FIG. 11 is provided merely for illustration, and any suitable ordering of layers may be used. That is, when multiple magnetic components (or portions thereof) are integrated into a laminate panel, any ordering of the laminate layers may be used to achieve a desired sequence of the integrated magnetic components. In some embodiments, the configuration of the layers and components formed thereon may be selected based, at least in part, on design considerations for optimizing one or more system and/or imaging parameters including, but not limited to, power consumption, gradient linearity, $B_0$ field homogeneity, gradient strength, RF strength, thermal considerations, etc. For example, in some embodiments, one or more layers comprising all or a portion of one or more $B_0$ coils may be located as the innermost layer(s) of the laminate panel to reduce power consumption of the low-field MRI system. In some embodiments, one or more outer layers of the laminate panel may be patterned to provide electromagnetic shielding. Accordingly, any ordering of layers of a laminate panel may be used, as the techniques described herein are not limited for use with any particular configuration in this respect.

As discussed above, though laminate panel 1100 is shown as having fabricated therein all or portions of $B_0$ coils, gradient coils, transmit/receive coils, shim coils, and electromagnetic shielding to illustrate exemplary components that may be fabricated using laminate techniques, a laminate panel may include any one or combination of components, or desired portions thereof. In some embodiments, at least some of the exemplary components are provided separate from laminate panel(s) (e.g., using conventional manufacturing techniques for those components). For example, some embodiments include laminate panel(s) having one or more $B_0$ coils formed thereon, with other components of the low-field MRI system being provided separate from the laminate panel(s). Other embodiments include laminate panels having one or more gradient coils formed thereon, with other components of the low-field MRI system being provided separate from the laminate panels. For example, in such embodiments, the main magnetic field $B_0$ for the low-field MRI system may be manufactured using conventional techniques, and the transmit/receive coil may be provided by a helmet-based and/or surface-based coil placed around or near the object to be imaged. In other embodiments, laminate panels may have formed thereon both one or more $B_0$ coils and one or more gradient coils (or portions thereof), with other components of the low-field MRI system being produced separate from the laminate panel(s).

Accordingly, it should be appreciated that laminate panels manufactured in accordance with techniques described herein may include any suitable number of layers on which any one or combination of low-field MRI components (or portions thereof) are formed, and such laminate panel(s) may be utilized in connection with any number of other laminate panel(s) or any one or combination of other components produced using other techniques, as the aspects are not limited in this respect. According to some embodiments, a hybrid approach may be used wherein one or more magnetic components are implemented with a portion being fabricated using laminate techniques and a portion produced using conventional techniques.

As discussed above, the inventors have recognized that low-field MRI systems, such as those described above and in the '652 application, may be combined with an electrophysiological measurement system, such as an EEG system, to provide a portable and/or lower-cost functional imaging system capable of performing patient-specific source localization of the electrophysiological measurements. Measurements of electrical activity within the body using one or more electrodes placed on the surface of the body have long been a valuable source of information for characterizing and diagnosing human biological processes. In EEG, electrodes are placed on the scalp and the electrical signals reflecting biological activity of neurons in the brain are measured. EEG measurements are safe and the technique is relatively easy to use even in very young children. EEG signals are thought to arise from the summation of the synchronous activity of thousands or millions of similarly-oriented neurons. In particular, EEG signals are believed to derive from pyramidal cells aligned in parallel in the cerebral cortex and hippocampus, which act as many interacting nonlinear oscillators, and thus can be used as an indicator of brain activity.

EEG signals conventionally represent electrical activity as a function of time. The temporal resolution of electrophysiological data acquisition including EEG can be on the order of milliseconds, such that neuronal events occurring over short timescales can be identified in the obtained signals. EEG signals may be obtained continuously over a period of time (e.g., 20-30 minutes) to detect the brain's spontaneous electrical activity. Alternatively, EEG signals time-locked to the repeated presentation of a stimulus may be obtained and a plurality of time periods (also called "epochs") corresponding to the time-locked signals may be averaged to study evoked potentials (EP) representing the brain's response to the presentation of the stimulus. In a clinical setting, EEG is often used to diagnose and/or monitor neurological diseases including epilepsy, stroke, sleep disorders, coma, tumors, and other focal-brain disorders by analyzing the spectral content of continuously-obtained EEG signals to determine changes in neuronal oscillations, which represent synchronized activity for networks of neurons in the brain.

Figure 3:
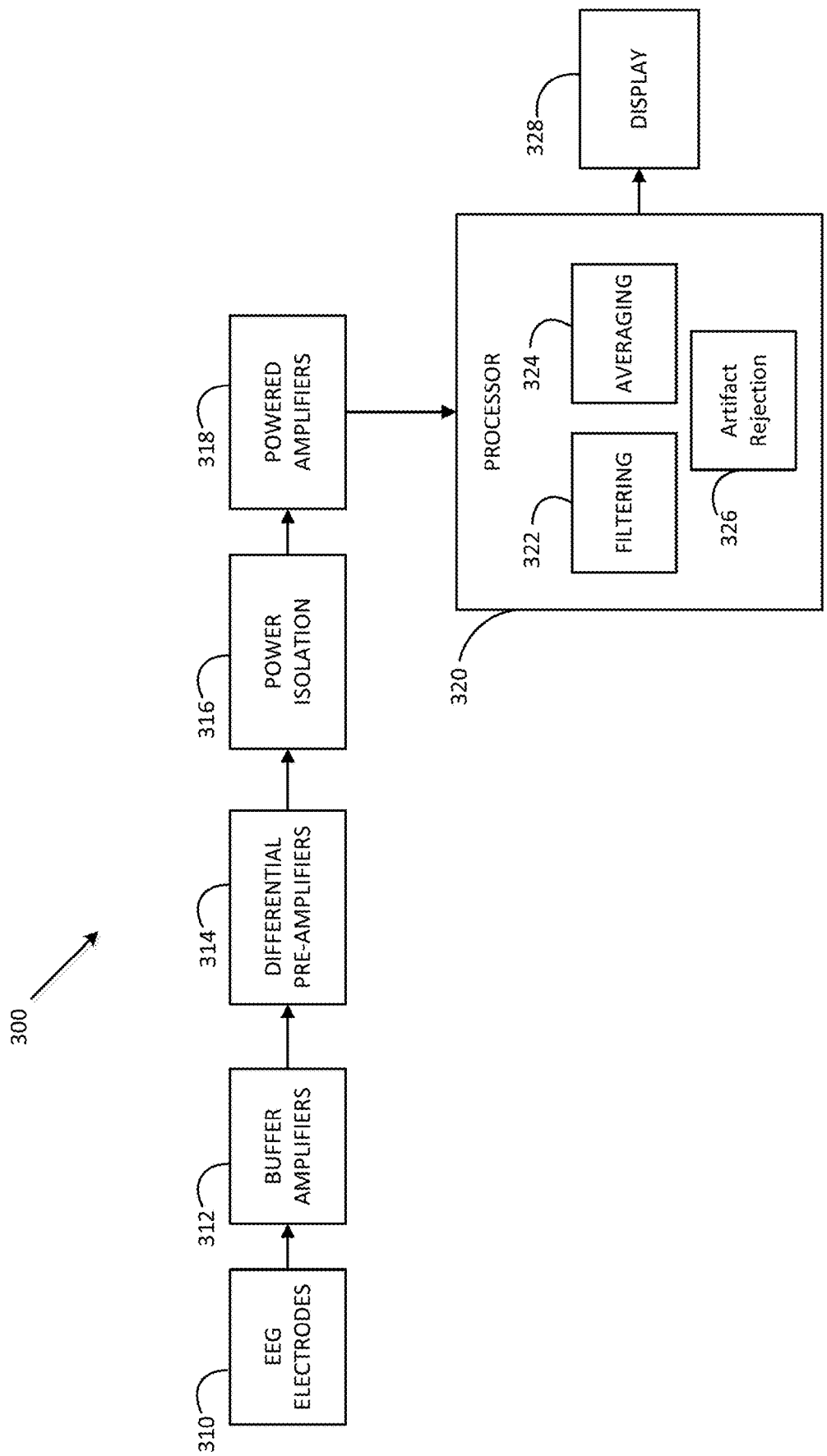
FIG. 3 illustrates components of an EEG system that may be used in accordance with some embodiments.

FIG. 3 illustrates a block diagram of an EEG system 300 that may be used in accordance with some embodiments. The EEG system includes a plurality of EEG electrodes 310 designed to be affixed to the surface of a patient's head and configured to obtain EEG data from the patient. Any suitable type of EEG electrodes including, but not limited to, metal ring-shaped electrodes, may be used. Frequently, the plurality of electrodes are sewn onto a stretchable cap which the patient may wear to facilitate placement of the electrodes on the patient's head. Any suitable number of electrodes may be used, and embodiments are not limited in this respect. Commercially-available EEG caps often include 32, 64, 128, or 256 electrodes, and are available in different sizes for patients with different size heads. The EEG electrodes are connected to system electronics, described in more detail below, by wires or "leads," which transmit the small EEG signals obtained by the electrodes to the EEG system electronics for amplification and processing.

EEG system 300 may include buffer amplifiers 312, which receive the output of the EEG electrodes. The buffer amplifiers operate to stabilize the obtained EEG signals and typically amplify them by a desired factor (e.g., a factor of two, five, ten, etc.) The buffer amplifiers 312 then provide the EEG signals to differential pre-amplifiers, which filter and may further amplify the EEG signals (e.g., by a factor of 2, 5, 10, 50, 100, etc.). EEG system 300 also includes power isolation components 316 configured to isolate the main power electronics of the EEG system from the patient to mitigate the possibility of accidental electric shock. Any suitable power isolation components including, but not limited to, optical isolation components may be used.

Powered amplifiers 318 may further amplify the EEG signals output from the differential pre-amplifiers 314 and convert the obtained analog EEG signals into digital signals for processing by processor 320. A/D conversion may then convert the signal for each electrode into a "channel" of EEG data that can be digitally processed. Processor 320 may be programmed to perform particular digital signal processing functions on the data in each EEG channel. The digital signal processing functions may include, but are not limited to, filtering 322, averaging 324, and artifact rejection 326, etc. EEG system 300 also may include display 328 configured to display the output of processor 320. For example, display 328 may be configured to display signal traces for each of the EEG channels, and the signal traces may be updated as the EEG data is being obtained.

EEG signals may also be used to perform source localization or estimation, which refers to the process of identifying locations of the brain that give rise to detected signals. Performing source localization provides spatial information about detected EEG signals. For example, source localization can be used to convert electrical signals obtained as a function of time to electrical signals as a function of space. The resulting electrical signals as a function of space can be presented as one or more images to facilitate visualization, analysis and/or further processing of the electrical activity of the brain. In general, source estimation or localization refers to any technique that provides spatial information regarding the location of the source of acquired electrophysiological data (e.g., EEG data). Determining a unique current source in the brain for a given EEG signal is typically not possible because some currents in the brain produce electric potentials that cancel each other out. To solve this "inverse problem," EEG source estimation techniques typically require making assumptions about the likely location and number of current sources in the brain to constrain the solution space and select among competing hypotheses. Because each patient's brain anatomy is different, an important assumption that facilitates accurate EEG source localization is determining an appropriate head model to use for generating a "forward solution." The forward solution represents the brain anatomy of a patient and is used to constrain solutions of the inverse problem to include only sources corresponding to the forward solution.

As discussed above, high-field magnetic resonance imaging (MRI) has been used to acquire structural brain data from which a patient-specific head model may be created. EEG source estimation or localization can then be performed with a higher degree of accuracy for the specific patient from which the EEG signals are obtained. However, despite the widespread clinical use of EEG systems, EEG source localization techniques are severely limited based on the cost and relative unavailability of MRI systems capable of capturing an MR image of patients on whom the EEG is obtained. Additionally, because most EEG systems include metal electrodes, they cannot be safely used in a high-field MRI scanner, further limiting the use of conventional high-field MRI in connection with EEG.

Moreover, as discussed in further detail below, EEG source localization requires the alignment of the EEG head coordinate system with the patient's MRI data to produce accurate source localization. The EEG head coordinate system is typically determined using a 3-D digitization system that captures spatial locations of multiple points on the surface of the patient's head prior to, during, or after collection of the EEG data. Alignment of the MRI data with the EEG head coordinate system is then achieved using manual co-registration of points on the patient's MRI with the digitized points in the EEG head coordinate system. Errors in the 3-D digitization and/or co-registration process result in EEG source localization errors. As discussed in further detail below, some embodiments are directed to a functional neuroimaging system including an integrated low-field MRI system and an electrophysiological measurement system, such as EEG, that facilitates the alignment of EEG data and MRI data.

Because MRI data of sufficient resolution was previously only available from high-field MRI scanners, the cost, lack of availability and other drawbacks associated with high-field MRI equipment prevented the use of MRI to perform source localization of electrophysiological measurements from being a feasible tool in most clinical situations, relegating its use instead to extraordinarily limited circumstances. Thus, the inventors' recognition that low-field MR systems may be configured for use in EEG source localization enables the provision of a relatively low cost electrophysiological imaging system, not previously available, that can be utilized in a wide variety of clinical diagnostic and therapeutic procedures. The inventors have appreciated that such systems also open up the possibility of developing control systems based on obtained electrophysiological data.

Figure 4:
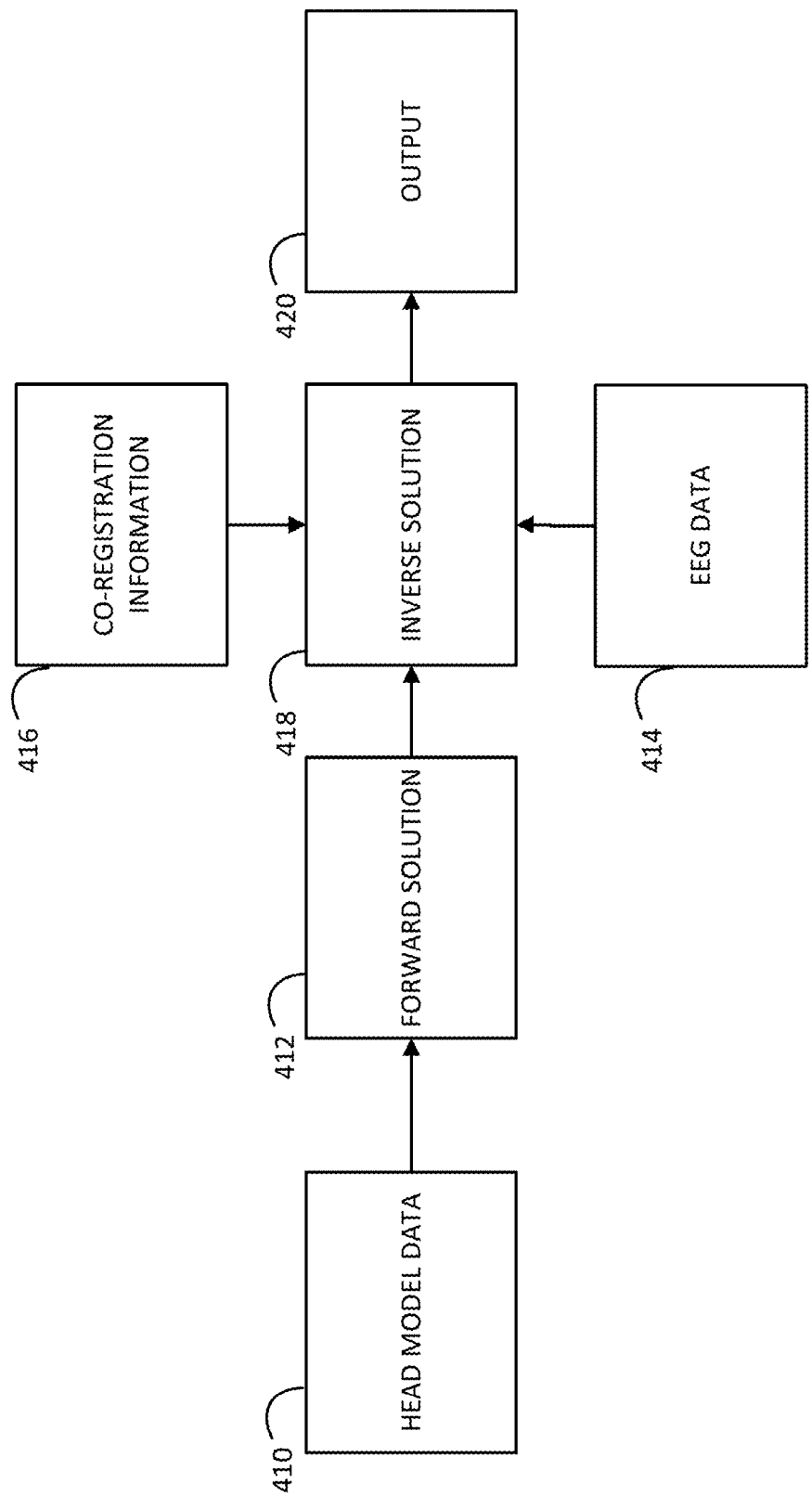
FIG. 4 illustrates a process for performing EEG source localization in accordance with some embodiments.

FIG. 4 illustrates a process for performing source localization of electrophysiological measurements, in accordance with some embodiments. While the following description is provided in the context of EEG data, it should be appreciated that the same techniques can be used to perform source localization (e.g., obtain spatial information regarding obtained data) on any type of electrophysiological data, including EEG, ECG, EMG, EOG or any other type of electrophysiological data, as the techniques are not limited for use with any particular type of data. For example, MR data may be used to constrain the inverse problem so that spatial information may be obtained from any of various types of electrophysiological data.

In act 410, head model data is acquired using a low-field MRI device. Any low-field MRI device capable of producing an image of satisfactory resolution for performing electrophysiological source localization may be used, and embodiments are not limited in this respect. For example, any of the low field MRI systems or configurations described in the '652 application may be used, or any other suitable system or configuration for providing low-field MR data may be used, as source localization of electrophysiological measurements is not limited for use with any particular low-field MR apparatus. In some embodiments, the low-field MRI device is configured to produce an image of a resolution higher than or equal to an in-plane resolution of three millimeters. Such a resolution may enable discerning of the layers of the boundary element model or other source space model used for electrophysiological source localization. In some embodiments, the low-field MRI device is configured to produce an image having a resolution of 3×3×3 millimeters isotropic. In other embodiments, the low-field MRI device is configured to produce an image having a resolution of 1×1×1 millimeters isotropic. However, other resolutions (both isotropic and anisotropic) may be used, as the techniques described herein are not limited for use with any particular resolution or range of resolutions.

The process then proceeds to act 412, where the head model data is used to generate a forward solution. Any suitable forward solution may be used including, but not limited to, a forward solution based on a spherical model, a boundary element model (BEM), a finite element model (FEM), or a finite difference method (FDM). In some embodiments, a BEM having at least three layers is used to model the skull, cerebrospinal fluid (CSF), and the brain surface, each of which may be modeled as having different tissue conductivities.

The process then proceeds to act 414, where EEG data is collected. Any suitable type of EEG system may be used, and embodiments are not limited in this respect. In some embodiments, an EEG system having components similar to those described above with regard to FIG. 3 may be used. In some embodiments, at least some of the electronics used for the EEG system may be shared with the low-field MRI system to produce an integrated system that is compact and lower cost than providing the EEG system and the MRI system separately. Because there are no safety concerns using metal EEG electrodes with a low-field MRI device, standard conventional EEG systems that include such electrodes may be used further reducing the cost of the system and improving the deployability of some embodiments.

The process then proceeds to act 416, where co-registration information is obtained. The co-registration information may be obtained in any suitable way using any suitable type of registration system. For example, the co-registration information may be obtained using a conventional 3-D digitization system, as discussed above. In some embodiments, the co-localization of the low-field MRI device and the EEG system provides for co-registration techniques not possible with conventional EEG systems. For example, in some embodiments the co-registration information may be obtained directly by the low-field MRI system itself before, during, or after obtaining of the EEG data. As discussed in more detail below, direct acquisition of the co-registration data by the low-field MRI device may facilitate the correction of artifacts including, but not limited to, patient motion.

The process then proceeds to act 418, where the inverse solution for localizing EEG sources in the brain of the patient is determined based, at least in part, on the forward solution, the EEG data, and the co-registration information. Any suitable technique or techniques may be used to determine the inverse solution. For example, in some embodiments, sources in the brain giving rise to the obtained EEG signals on the scalp are modeled as one or more electric dipoles. The process then proceeds to act 420, where the source localization results are output. For example, an image of the patient's brain as captured using the low-field MRI device may be displayed on a display, and one or more EEG sources (e.g., electric dipoles) corresponding to the solution of the inverse solution may be shown overlaid on the displayed image.

In some embodiments, the EEG source analysis may be used to characterize particular neurological disease states (e.g., Parkinson's syndrome, schizophrenia, traumatic brain injury, stroke, Alzheimer's disease, etc.). For example, one or more neurological conditions may be characterized by temporal and/or spatial correlations observed in the EEG data and/or the EEG source analysis, and an EEG "signature" or "signatures" template corresponding to the neurological disease state may be stored in a library of disease states. The library of disease states may be used as an assessment tool in analyzing and characterizing EEG data collected from a patient by finding the closest match to the template in the library. Such a technique would enable EEG-based "fingerprinting" providing physicians with a useful tool in diagnosing and/or monitoring neurological diseases.

According to some embodiments, clustering techniques (e.g., statistical clustering techniques such as K-means, Gaussian mixture models (GMMs), support vector machines (SVMs), etc.) may be used to cluster and classify EEG images obtained via the techniques described herein or information derived from such images that are known to correspond to various states of interest (e.g., any of various healthy or diseased states for which clustering and classification is desired). The resulting clusters may be labeled and used as a model for later classifying new EEG images (or information derived therefrom). For example, new EEG data may be compared to the model to characterize the EEG data relative to the clusters captured by the model to evaluate similarities/dissimilarities between the EEG data and the known states associated with the modeled clusters. Such classification can be used to characterize obtained EEG data as diseased or healthy, to assist in identifying various neurological disorders, or to otherwise classify functional neuroimaging data.

As discussed briefly above, in some embodiments, a low-field MRI device may be configured to determine co-registration information for spatially aligning obtained EEG data with a patient's MRI data obtained by the MRI device. For example, the EEG system may include one or more markers that can be placed on the patient's head, and the low-field MRI system may be configured to determine a spatial position of the one or more markers to define the EEG head coordinate system. Any suitable marker(s) detectable by the low-field MRI system may be used. In some embodiments, at least one of the markers is an EEG electrode used to obtain EEG data. Additionally, or alternatively at least one of the markers may be separate from the EEG electrodes used to obtain EEG data. The marker(s) may be placed at any suitable location on the patient's head including, but not limited to, locations such as the inion or nasion and the left and right pre-auricular points, which are typically digitized using a conventional 3D digitizer to define the EEG head coordinate system.

In embodiments where the low-field MRI device is configured to determine co-registration information by detecting one or more markers, the co-registration information may be obtained at any suitable time and/or at any suitable frequency. For example, the co-registration information may be continuously determined during an MRI scan by the low-field MRI device. Alternatively, the co-registration information may be determined periodically or in response to a user input to instruct the MRI system to determine the co-registration information.

Typically, when EEG data is combined with high-field MRI data, the EEG data and the high-field MRI data are obtained using different systems that do not communicate with each other. An integrated EEG and low-field MRI system, in accordance with some embodiments, provides communication and control benefits not possible with conventional EEG or MRI systems which obtain data in isolation. For example, data obtained using the EEG system may be used to modify one or more parameters of the low-field MRI system and/or the MRI data obtained using the low-field MRI system may be used to modify one or more acquisition parameters of the EEG system. Such feedback may inform the functional neuroimaging process to ensure that the data obtained is of sufficient quality to perform accurate EEG source localization. In addition, integrating low-field MR and EEG in a single system significantly simplifies the process and workflow and is significantly more convenient for patient and physician. For example, one or more of field of view, signal-to-noise ratio, resolution, etc. may be modified based on obtained EEG data. For example, EEG data may be used to identify a particular portion of anatomy at which to acquire further MR data and/or to acquire MR data at a higher resolution and/or SNR.

An EEG system may include one or more components (e.g., metal EEG electrodes) that when placed inside of the low-field MRI device are likely to perturb the homogeneity of the $B_0$ field causing it to become less homogeneous. In some embodiments, the $B_0$ field of the low-field MRI device may be modified to improve the homogeneity of the $B_0$ field in the presence of the metal component(s) of the EEG system. For example, the low-field MRI device may include shimming elements (e.g., shim coils) that may be appropriately positioned and/or activated to correct the field distortion introduced by the metal component(s) to improve the homogeneity of the $B_0$ field. Any of the static or dynamic shimming techniques and/or field sensing techniques described in the '652 patent may be utilized to adjust the $B_0$ field to achieve desired field strength and homogeneity for the particular environment and loading conditions in which the MRI system is operating such as those that may arise when operating a low-field MRI system in the presence of one or more other electrophysiological measurement devices, such as EEG.

According to some embodiments, one or more characteristics or parameters of the low-field MRI system may be modified based, at least in part, on an EEG source localization result. For example, initial MRI data obtained by the low-field MRI device may be used to create a forward model, and the forward model may be used for EEG source localization, as discussed above. Depending on the EEG source localization result, one or more characteristics or parameters of the low-field MRI device may be modified and additional MRI data may be obtained by the low-field MRI device. This process may be repeated until an EEG source localization result of a desired quality is obtained. Any metric or metrics may be used to determine whether an EEG source localization result is of a desired quality, and embodiments are not limited in this respect.

Because the EEG system and the low-field MRI device are co-located and in communication with one another, in some embodiments, EEG source localization may be performed in essentially real-time using the obtained MRI data and EEG data. The EEG source localization process may be fully or partially automated to enable one or more EEG sources to be localized in the brain of a patient without or with minimal human intervention.

As discussed above, the integration of a low-field MRI device and an EEG system in accordance with some embodiments, enables one or more scanning parameters of the low-field MRI device to be modified based, at least in part, on information from the EEG system. Additionally, the integration may also enable information obtained by the low-field MRI device to modify one or more acquisition parameters of the EEG system. For example, the low-field MRI device may be configured to detect motion of an imaged patient, and the EEG system may be configured to discard at least some obtained EEG data based, at least in part, on the detected motion. The determination of whether to discard EEG data may be made based, at least in part on whether the amount of detected patient motion is greater than a threshold value. In some embodiments, the EEG data obtained during detected patient motion may be associated with an identifier, but may not actually be discarded.

In some embodiments, the EEG system may be configured to detect patient motion and at least one scanning parameter of the low-field MRI device may be modified based, at least in part, on the detected patient motion. For example, the low-field MRI device may be configured to discard at least some obtained MRI data in response to the detected patient motion and MRI data corresponding to the discarded MRI data may optionally be automatically re-acquired. Information other than patient motion may additionally or alternatively be detected by the EEG system, the low-field MRI device, or both systems to provide feedback that modifies how one or both of the systems acquire data, and patient motion is described as an example.

Figure 5:
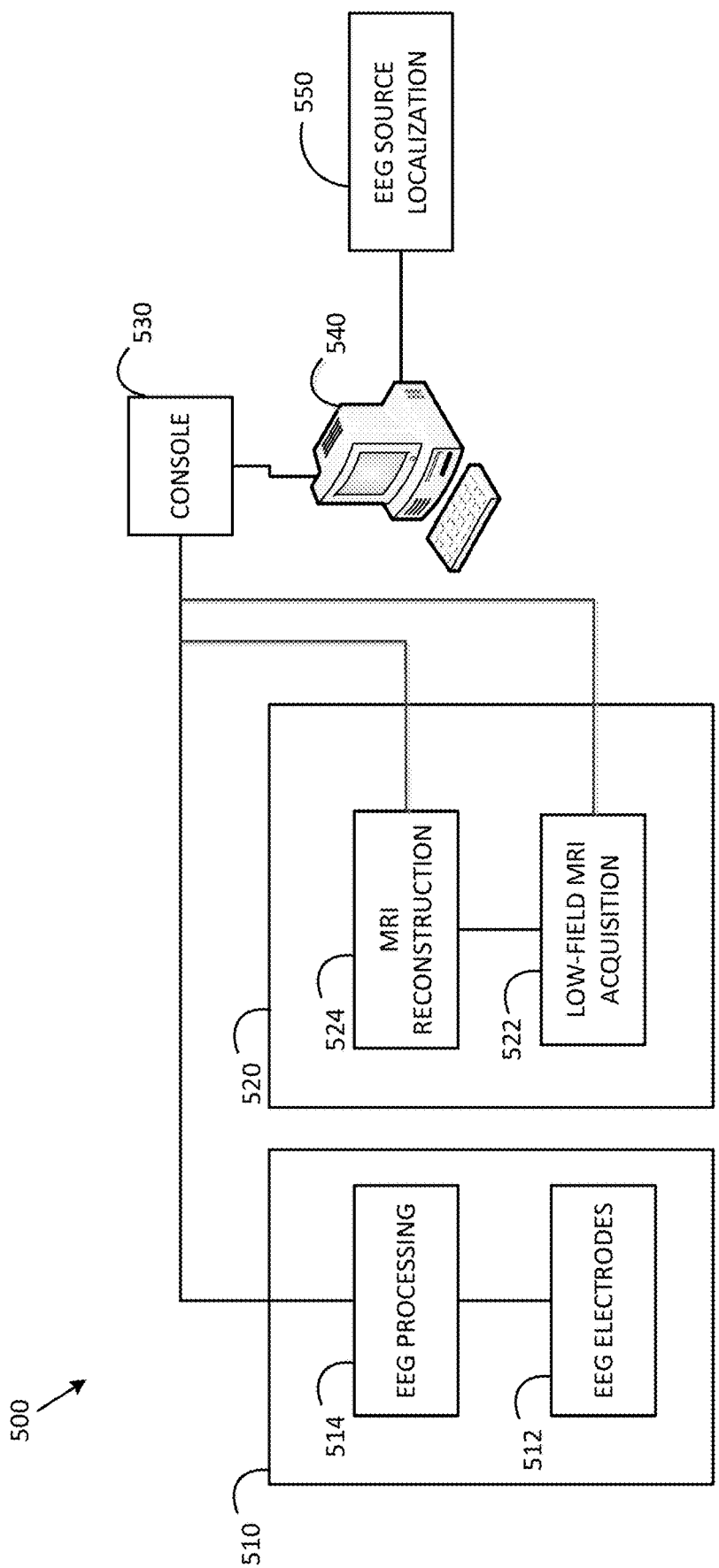
FIG. 5 schematically illustrates an integrated functional imaging system in accordance with some embodiments.

FIG. 5 schematically illustrates components of an integrated functional neuroimaging system 500 in accordance with some embodiments. System 500 includes EEG system 510 and low-field MRI system 520. FIG. 5 shows EEG system 510 operatively connected to low-field MRI system 520 via console 530. However, it should be appreciated that the EEG system and the MRI system may be connected in any other suitable way including, but not limited to, being directly connected by one or more communications cables configured to transmit information between the systems.

EEG system 510 includes EEG electrodes configured to acquire EEG data. The acquired EEG data is sent to EEG processing component 514, where the acquired EEG data is processed by, for example, filtering, amplifying, averaging, etc., as discussed above in connection with the illustrative EEG system shown in FIG. 3. EEG system 510 may include other components not shown in FIG. 5 including, but not limited to, the EEG components shown in FIG. 3.

Low-field MRI system 520 includes low-field MRI acquisition components 522 configured to acquire low-field MRI data. Low-field MRI acquisition components 522 may include, but are not limited to, magnetics for producing a $B_0$ field, gradient coils, control electronics, temperature control (e.g., cooling) systems, amplifiers, electromagnetic shielding, operating power systems, and RF coils configured to perform one or both of transmitting RF energy and detecting RF echoes. Any suitable low-field MRI device configuration may be used including, but not limited to, a bi-planar configuration (e.g., as shown in FIG. 1) and a solenoid configuration. MRI data acquired by low-field MRI acquisition components 522 is sent to MRI reconstruction component 524, where an MR image is reconstructed based, at least in part, on the obtained MRI data. In some embodiments, functional neuroimaging system 500 includes at least one additional receive coil (not shown) to enable active noise cancellation. Any suitable type of additional receive coil may be used, and embodiments are not limited in this respect.

Functional neuroimaging system 500 also includes console 530, which may include one or more processors programmed to generate MRI pulse sequences used to acquire data using low-field MRI system 520 and/or issue control instructions to EEG system 510. Additionally, console 530 may be configured to perform any other suitable operation. In some embodiments, console 530 may be configured to receive MR data detected by one or more receive coils of low-field MRI system 520 and provide the received MR data to workstation 540 for processing the data (e.g., to reconstruct one or more MRI images). In some embodiments, console 530 may be configured to receive obtained EEG data and/or co-registration information in addition to MR data, and workstation 540 may be programmed to process the obtained MR and EEG data to perform EEG source localization 550.

Aspects of the EEG system 510 and low-field MRI system 520 may be integrated in any suitable way to provide benefits not achievable using separate conventional EEG and low-field MRI systems. For example, the integration of the EEG system and the MRI system may include sharing of one or more hardware and/or software resources. For example, in some embodiments, at least a portion of the power and/or control electronics used to acquire EEG data and MRI data may be shared to reduce the footprint of the integrated system for improved portability. Additionally, system 500 includes several processing components configured to perform different processing functions including EEG processing, MRI reconstruction, and EEG source localization. In some embodiments, some or all of these processing functions may be implemented by one or more shared processors programmed to perform the functions. In some embodiments, some or all components of the integrated functional imaging system are disposed on a cart to improve portability of the system.

In some embodiments, some or all of the components in EEG system 300 shown in FIG. 3 may be integrated with console 530. For example, the EEG processing signal chain may be implemented using components of console 530 rather than being provided separately as shown in FIG. 5. Accordingly, some embodiments are directed to an integrated system comprising at least one component configured to perform both MRI processing and EEG processing to provide a compact functional neuroimaging system with reduced power requirements. For example, signal input and/or outputs (I/O) for both MRI and EEG may be provided by and implemented on a single "board" and integrated with a single system for performing EEG-based imaging. In this context, a control board may be implemented with a controller and I/O capabilities to control operation of both MR and EEG devices, or certain portions thereof in the MR and EEG signal chain.

The above-described functional imaging system combines EEG and low-field MRI imaging modalities to provide spatiotemporal functional neuroimaging data that can be used to diagnose and monitor any of a large number of neurological disease states. The inventors have recognized and appreciated that the portability of some low-field MRI systems enables the integration of any of a number of physiological measurement systems with low-field MRI to produce a functional imaging system. For example, in some embodiments, a low-field MRI device is integrated with one or more electrophysiological measurement systems including, but not limited to, an EEG system, an electromyography (EMG) system, an electrooculography (EOG) system, and an electrocardiography (ECG) system. In some embodiments, a low-field MRI system is integrated with an optical imaging system. In yet other embodiments, a low-field MRI system is integrated with an ultrasound imaging system. In some or all embodiments comprising a low-field MRI system integrated with a physiological measurement system, the low-field MRI system and the physiological measurement system may be configured to simultaneously acquire MRI data and physiological data. According to some embodiments, MR data and electrophysiological data is acquired serially, either by interleaving the acquisition or performing acquisition of MR data followed by acquisition of EEG data or vice versa.

When MR data is acquired simultaneously with electrophysiological data, operation of the MR device can produce artifacts in acquired electrophysiological data. For example, gradient coil switching and/or radio frequency (RF) switching can cause spikes to appear in the electrophysiological data (e.g., EEG data). Such artifacts may be removed or suppressed using software and/or the MR pulse sequence can be used to assist in removing artifacts. For example, because the pulse sequence defines the timing of gradient and RF switching, this information can be used to identify and remove artifacts in acquired electrophysiological data. Noise or artifacts resulting from operation of the MR device can be removed in other ways, as the aspects are not limited in this respect.

The functional neuroimaging system described above may also be used in combination with Overhauser-enhanced MRI (OMRI) to obtain information on free radicals, either endogenous or via contrast agents introduced to the patient being imaged. The data from the different modalities (e.g., EEG, MRI and/or OMRI) may be combined, registered or otherwise utilized to provide rich data on a patient's brain for use in a variety of applications including disease characterization, diagnostics, behavior maps, trauma assessment, visualization of brain activity (e.g., in repose or resting, in response to stimuli, cognitive activity, drugs, etc.). Such an integrated neuroimaging system can provide multi-modal data that is otherwise unavailable.

Figure 6C:
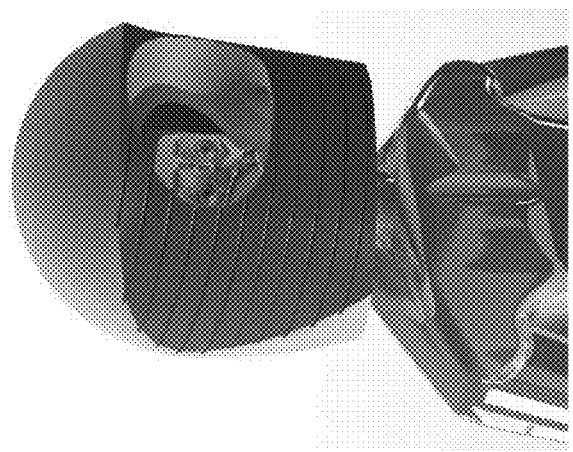
FIGS. 6A-6C illustrate brain imaging helmets that can be used to integrate low-field MRI with one or more electrophysiological modality.
Figure 6B:
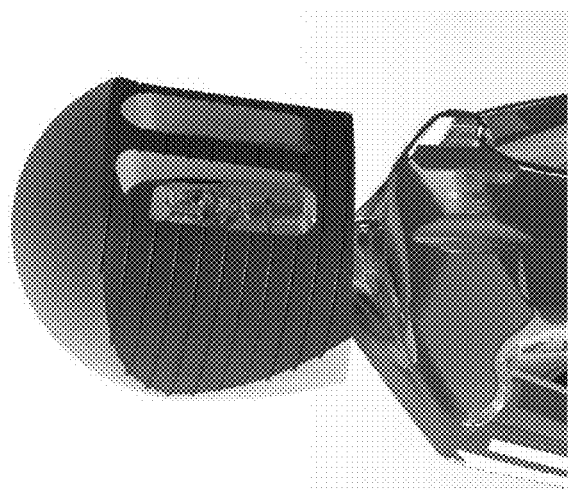
Figure 6A:
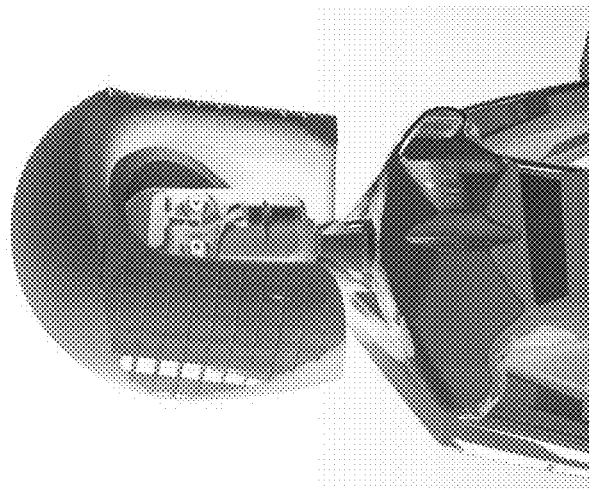

FIGS. 6A-C illustrate brain imaging helmets for low-field MRI configured that can be used in conjunction with other electrophysiological measurements such as EEG to provide an integrated neuroimaging device. The helmets may include a $B_0$ magnet in a solenoid geometry about the surface of the helmet to produce a $B_0$ field in an axially direction through the head (i.e., from the top of the head to the bottom or vice versa.) The helmets may further have incorporated therein a gradient system having one or more gradient coils and an Rx/Tx coil array from excitation and detection, or one or more of the magnetics component may be provided separately.

In the embodiment illustrated in FIG. 6A, the magnetics are arranged for full clearance of the patient's face and is therefore the most open of the three configurations. In the embodiment illustrated in FIG. 6B, one or more magnetics components necessitate partial blockage of the face (e.g., multi-channel or single-channel RF coil elements and/or $B_0$ windings may need to be provided in this area to meet particular design requirements. In the embodiment illustrated in FIG. 6C, openings remain around the patient's eyes to minimize claustrophobic effects, but one or more magnetics components are housed within the helmet in the front portion over the patient's mouth area. The neuroimaging helmets provide relative freedom of the user's hands, allowing for neuroimaging to be conducted while a user performs one or more desired tasks, manipulates objects and/or makes selections on a computer screen via mouse or touch screen, opening up a wealth of new possibilities with respect to functional brain imaging.

As discussed above, the inventors have recognized that low-field MRI can be utilized to assist in therapeutic procedures (e.g., one or more surgical procedures), for example, procedures that benefit from image guidance techniques. As used herein, therapy refers to any procedure used to perform a treatment. Therapeutic procedures include, but are not limited to, high intensity focused ultrasound (HIFU), optical procedures such as laser therapies, x-ray therapy procedures, transcranial magnetic stimulation (TMS), etc. Therapeutic procedures typically involve a corresponding therapeutic device, for example, an ultrasound device, a laser device, an x-ray device, a TMS coil, etc. Low-field MR facilitates the use of one or more therapeutic devices in conjunction with MR.

As discussed above, the significantly lower field strengths of low-field MRI allow for open geometries that facilitate access to the patient by a surgeon performing a procedure. For example, the bi-planar geometry illustrated in FIG. 1 allows for a patient to be placed between the bi-planar coils for imaging and permits access to the patient by a clinician. Any of the low-field MRI systems described in the '652 application may be used in this respect. For example, FIGS. 7, 8A, 8B, 9A and 9B illustrate exemplary bi-planar configurations that may be suitable for use in conjunction with one or more surgical procedures, as discussed in further detail below.

In addition, the low field strengths involved in low-field MR allow for a wider variety of instrumentation to be used in proximity to the MR equipment. For example, any of various therapeutic devices that cannot be operated in proximity to a high-field MRI system may be operated in conjunction with a low-field MR device. Techniques for suppressing noise in the environment of a low-field MR device described in U.S. application Ser. No. 14/845,949 ('949 application), titled "Noise Suppression Methods and Apparatus," filed on Sep. 4, 2015, which is herein incorporated by reference in its entirety, can be utilized to facilitate the use of one or more therapeutic devices in conjunction with a low-field MR device. In particular, noise or disturbances caused by one or more therapeutic devices can be detected, characterized and suppressed using the techniques described therein.

Figure 7:
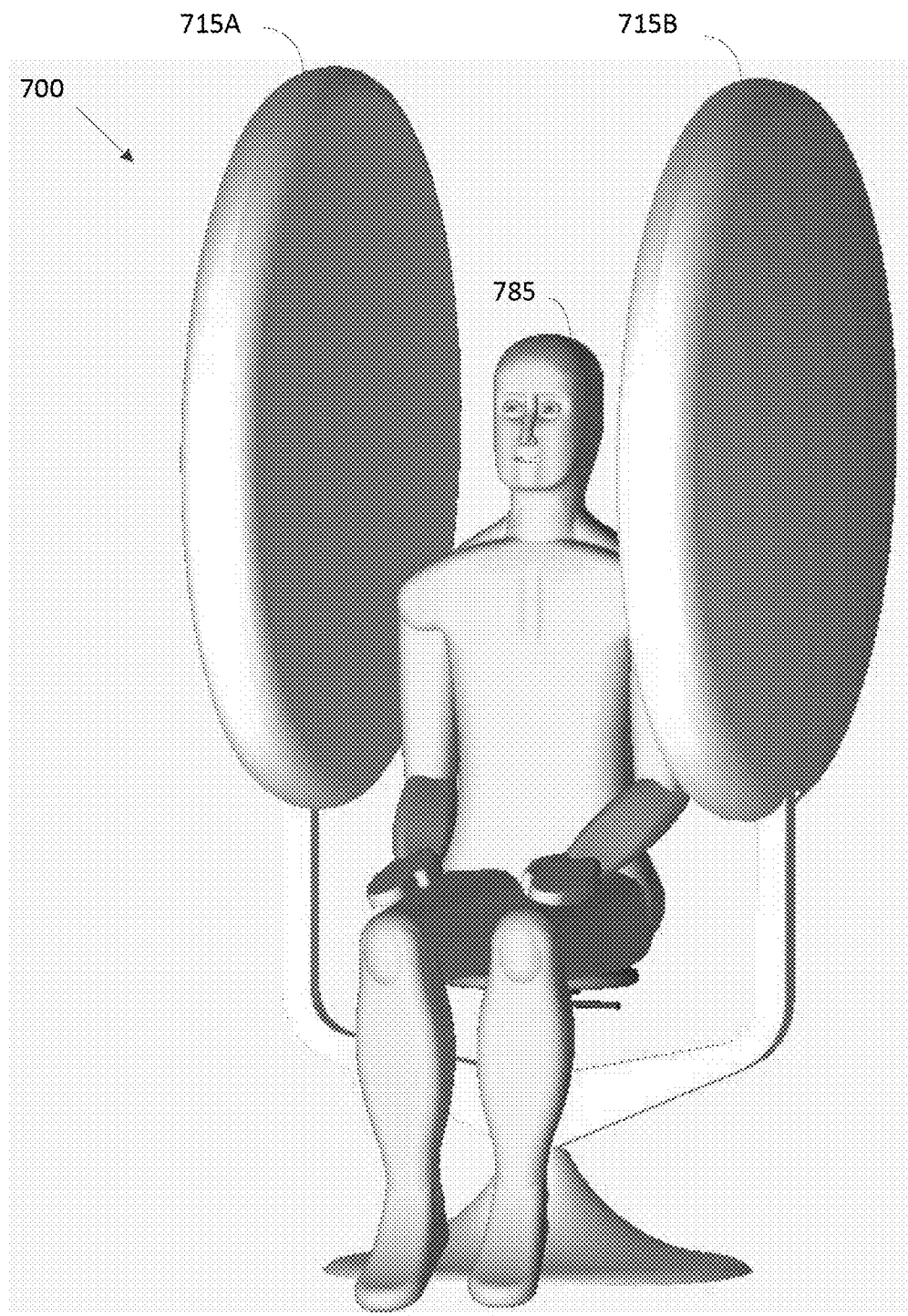
FIG. 7 illustrates an exemplary seated bi-planar low-field MRI system for use in conjunction with one or more other modalities.

FIG. 7 illustrates system 700 showing a patient 785 seated within the field of view of bi-planar magnets 715A and 715B comprising magnetics components configured to perform low-field MRI with an outer covering or housing, which may further comprise other components such as internal shielding, electrical connections, power and control electronics, etc., and which may generally provide a measure of environmental protection for low-field magnetics components (e.g., B0 magnet, gradient coils, transmit/receive coils, etc.).

Figure 8A:
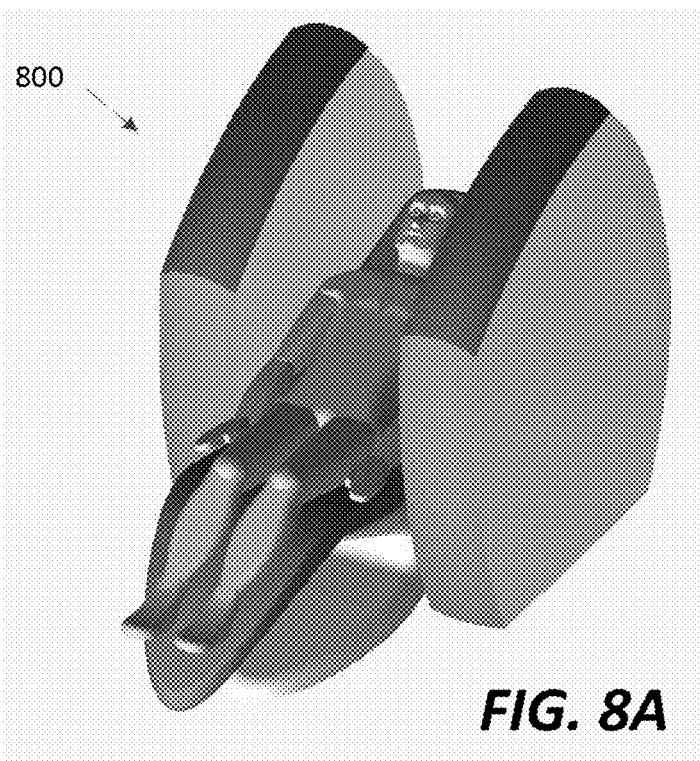
FIGS. 8A and 8B illustrate exemplary reclining bi-planar low-field MRI systems for use in conjunction with one or more other modalities.
Figure 8B:
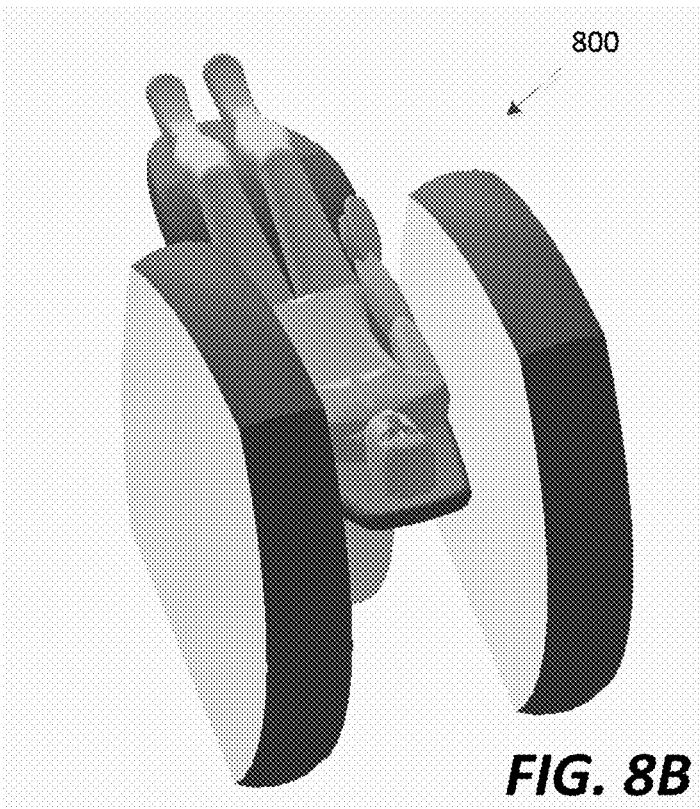

FIGS. 8A and 8B show a system 800 having a reclining configuration in which the magnetics components 810A and 810B are arranged within an frame comprising a seating portion 835 adjustably oriented at an angle to accommodate a patient being placed between the magnetics components in a reclined position. The reclining portion of the system may be adjustable to facilitate a desired positioning of the patient between the magnetics components so that the desired portion of the patient is located within the field of view of the magnet. Additionally or alternatively, the magnetics components may be adjustable within enclosure 815 to provide additional flexibility in positioning the magnetics relative to the patient. Magnetics components 810A and 810B may be connected via one or more suitable cables to power electronics, which may be mounted on a rack or housed with another suitable transportable structure to facilitate the portability of the MRI system. These example systems are generally open at facilitate more convenient access to the patient by a surgeon performing a procedure.

Figure 9A:
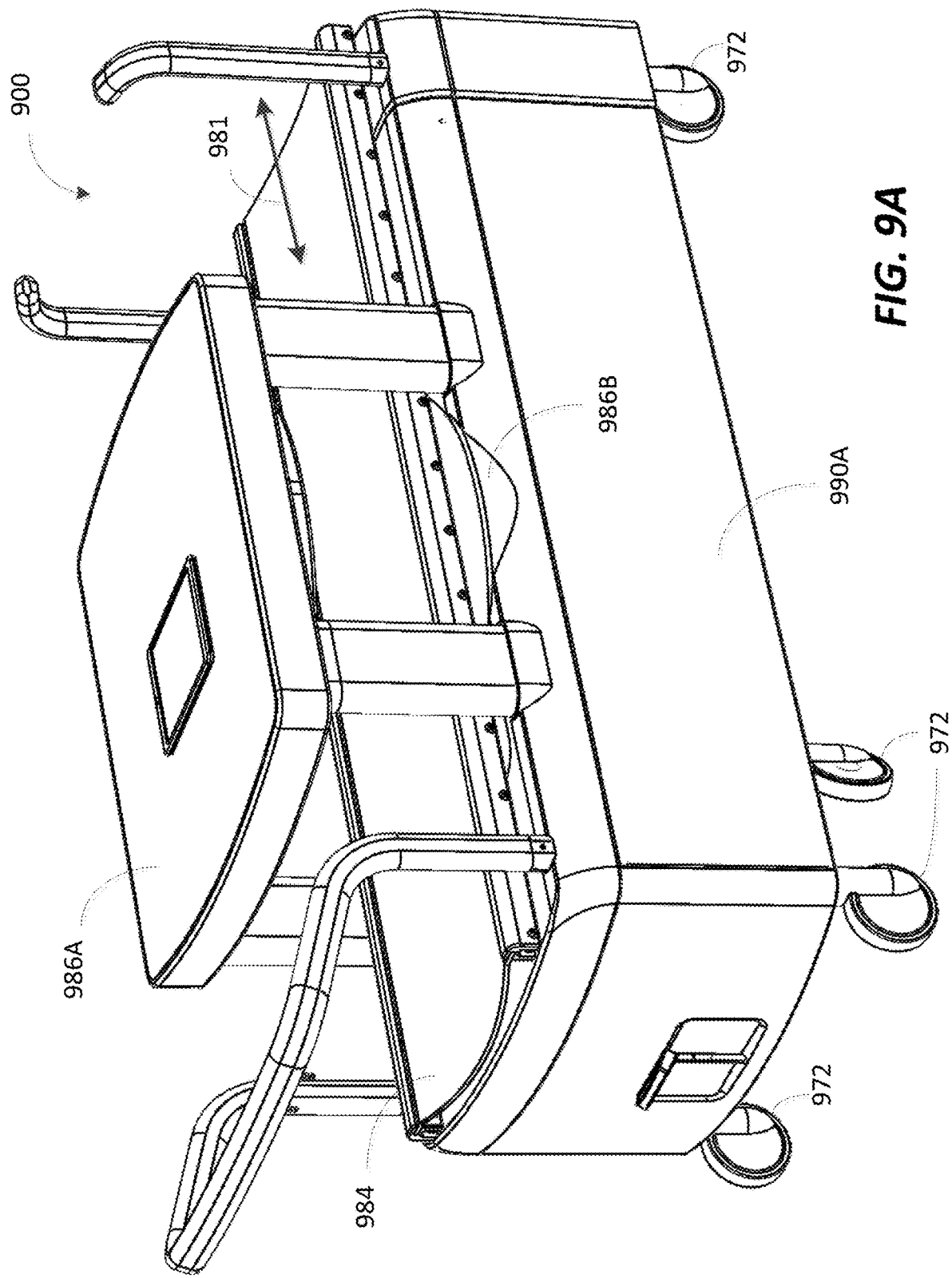
FIGS. 9A and 9B illustrate a transportable low-field MRI system, in accordance with some embodiments.
Figure 9B:
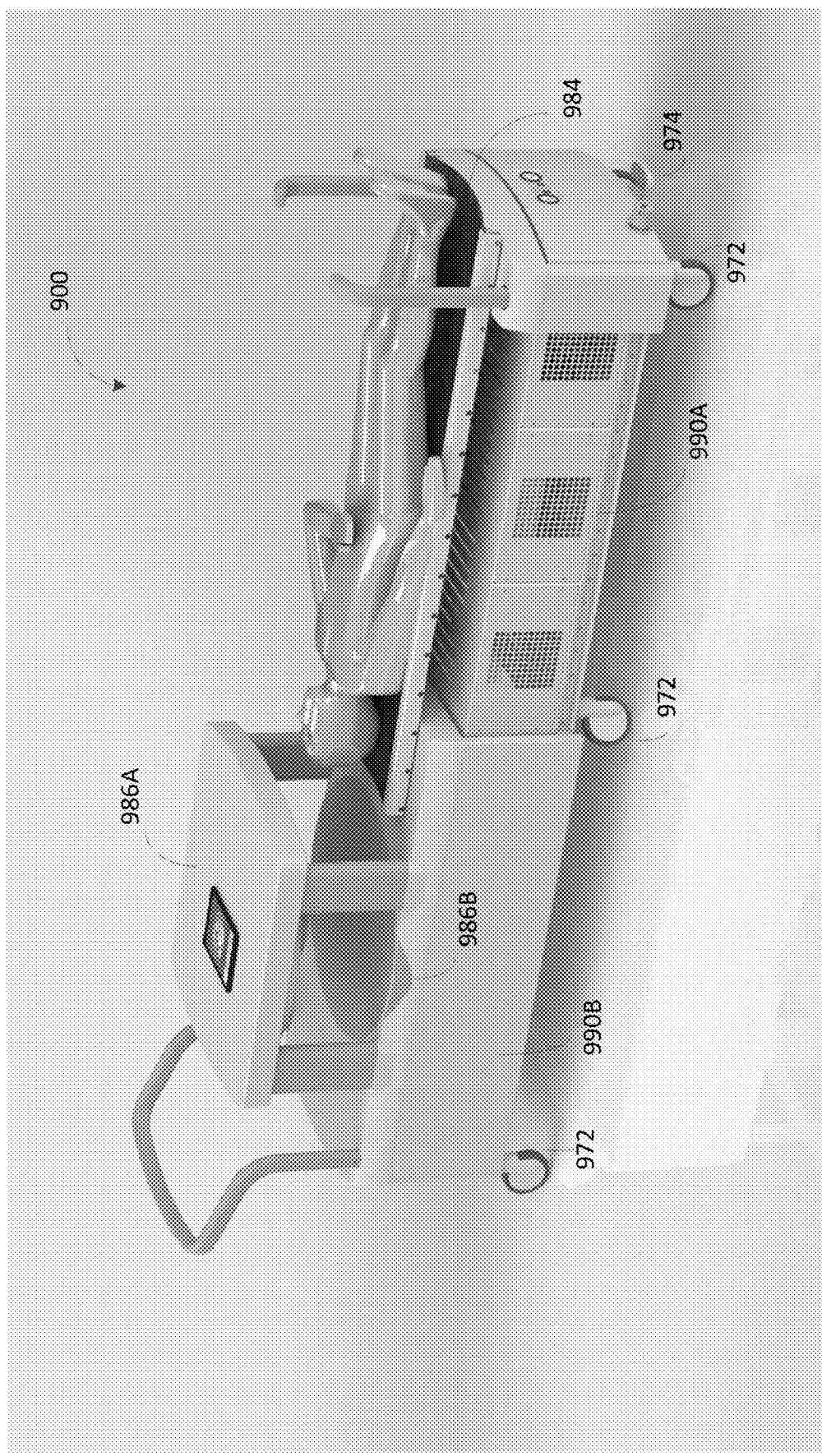

FIGS. 9A-9B illustrate a portable or cartable low-field MRI system 900 suitable for use in performing techniques described herein, in accordance with some embodiments. System 900 may include magnetic and power components, and potentially other components (e.g., thermal management, console, etc.), arranged together on a single generally transportable and transformable structure. System 900 may be designed to have at least two configurations; a configuration adapted for transport and storage, and a configuration adapted for operation. FIG. 9A shows system 900 when secured for transport and/or storage and FIG. 9B shows system 900 when transformed for operation. System 900 comprises a portion 990A that can be slid into and retracted from a portion 990B when transforming the system from its transport configuration to its operation configuration, as indicated by the arrows shown in FIG. 9B. Portion 990A may house power electronics, console (which may comprise an interface device such as a touch panel display) and thermal management. Portion 990A may also include other components used to operate system 900 as needed. The transportable system includes castors or wheels 972 to allow the system to be rolled to a desired location and a brake 974 (see FIG. 9B) to fix the system when the desired location is reached.

Portion 990B comprises magnetics components of low-field MRI system 900. When transformed to the configuration adapted for operating the system to perform MRI (as shown in FIG. 9B), supporting surfaces of portions 990A and 990B provide a surface on which the patient can lie. A slide-able bed or surface 984 may be provided to facilitate sliding the patient into position so that a portion of the patient to be imaged is within the field of view of the low-field MRI magnetics components. System 900 provides for a portable compact configuration of a low-field MRI system that facilitates access to the device in circumstances where it conventionally is not available.

FIGS. 9A-9B illustrate an example of a convertible low field MRI system that utilizes a bi-planar magnet forming an imaging region between housings 986A and 986B. Housings 986A and 986B house magnetics components for the convertible system 900. According to some embodiments, the magnetics components may be produced, manufactured and arranged using exclusively laminate techniques, exclusively traditional techniques, or using a combination of both (e.g., using hybrid techniques). The convertible low-field MRI system 900 allows the system to be brought to the patient to facilitate operation in a wide variety of circumstances. As discussed above, due at least in part to the low-field strengths, one or more electrophysiological sensors may be coupled to the patient to obtain electrophysiological data and one or more controllers may be disposed within convertible system 900 to control data acquisition. For example, the patient may wear an EEG cap or head unit having a plurality of electrodes configured to obtain EEG data from the patient while positioned within the field of view of system 900. A controller (or multiple controllers) of system 900 may be configured to obtain MR data and electrophysiological data and utilize the MR data to provide spatiotemporal electrophysiological data, for example, one or more functional spatiotemporal EEG, EKG, EMG, EOG images, etc.

The inventors have appreciated that an exemplary therapeutic procedure that may benefit from low-field MRI is high intensity focused ultrasound (HIFU), which involves applying high-intensity focused ultrasound energy to specific locations to ablate tissue (i.e., by heating and destroying target tissue such as a tumor). MRI has been used to guide this procedure to ensure that the HIFU energy is being applied to diseased and not healthy tissue to reduce or mitigate collateral tissue damage to the extent possible. As discussed above, using low-field MRI instead of high-field MRI allows open configurations to be used to provide significantly improved access to the patient as well as to allow for a greater variety of tools and instruments to be utilized during the procedure due to the significantly lower field strengths.

The inventors have further appreciated that low-field MRI may have additional benefits in assisting and improving a HIFU procedure. For example, the relaxation time T1 in MR is dependent on temperature and can be used to monitor the temperature at the application site and proximate to the site of tissue ablation. By analyzing T1 times, an alert may be generated to warn a surgeon when temperatures are reaching unacceptable levels in the area of healthy tissue and temporarily suspend application of the ultrasound or adjust the location of the application to avoid damaging or destroying healthy tissue. Low-field MRI may be used to guide other surgical or therapeutic operations, including tissue ablation using other techniques such as focused radio frequency (RF) techniques, lasers or other optic techniques, x-ray techniques, etc., or in other therapies such as to facilitate placement of a TMS coil to perform a desired TMS treatment.

The inventors have further appreciated that Overhauser-enhanced MRI (OMRI) can be utilized at low-field strengths to detect free-radicals, which can be used as a guide to locating and ablating tissue having high concentrations of free radicals such as tumors. OMRI may also be used as an early detection mechanism to locate areas of high free radical concentrations, which may be indicative of angiogenic, metabolic or other tumor processes that can be detected at an early stage. Free radical detection via OMRI may also provide a measure of the efficacy of HIFU treatment as the tissue ablation processes destroys tissue and generates free radicals. Furthermore, contrast agents may be administered to improve the contrast of low-field MRI. The contrast agents may include drugs or compounds that begin the processes of tissue destruction and/or that promote free radical production. Following administration of a contrast agent, the site of tissue ablation may be located via OMRI or using low-field MRI without Overhauser-enhancement in one or more images to assist the surgeon in applying HIFU to the desired site of tissue ablation.

As discussed above, EEG-based neuroimaging may be deployed in control systems to control, at least in part, any number of systems or machines. For example, in the medical field, EEG functional data may be obtained and processed to understand a person's intent and/or otherwise characterize the individual's thoughts to control prosthetics, operate a wheel chair, etc. In the industrial fields, such neuroimaging control may be used to operate a vehicle or a portion thereof (e.g., an automobile, aircraft, military vehicle, etc.) and/or control a robotic "outfit" to allow human wearers to engage in activities that would otherwise be impossible (e.g., lifting heavy objects, transporting dangerous materials, etc.). Operation of many vehicles (and other machinery) already requires the operator to wear a helmet, and an integrated EEG/low-field MRI device may be incorporated into existing helmets or new helmets may be designed to include such an integrated neuroimaging device. In the business context, neuroimaging control may be used to operate a computer or to assist in using other electronic devices. Indeed, functional neuroimaging can be the basis for a variety of man-machine interfaces to facilitate control or operation of a machine or system. Functional neuroimaging may also be used as a monitoring mechanism as a check on a human operator, for example, to detect and alert a human operator (e.g., a driver) when it is detected that the operator has fallen asleep, or to otherwise detect and mitigate when an operator has entered other deleterious or unsafe brain states that put the safety of the operator or others at risk.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, a controller or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The invention claimed is:

1. A system, comprising:
a low-field magnetic resonance (MR) device comprising:
a magnetics system having a plurality of magnetics components configured to produce magnetic fields for performing magnetic resonance imaging, the magnetics system comprising:
a $B_0$ magnet configured to produce a $B_0$ field for an imaging region of the low-field MR device, the $B_0$ magnet comprising at least one first $B_0$ magnet and at least one second $B_0$ magnet, which are positioned in a bi-planar arrangement about the imaging region; and
at least one laminate panel comprising a plurality of laminate layers, each of the plurality of laminate layers including at least one non-conductive layer and at least one conductive layer patterned to form at least a portion of a gradient coil configured to produce a gradient magnetic field, wherein the at least one laminate panel comprises a first laminate panel comprising a first gradient coil and a second laminate panel comprising a second gradient coil, the first and second gradient coils of the first and second laminate panels being disposed on opposite sides of the imaging region;
a power system comprising one or more power components configured to provide power to the magnetics system to operate the low-field MR device to perform image acquisition, the one or more power components comprising at least one power component configured to provide power to the first and second laminate panels;
a base that supports the magnetics system and houses the power system; and
at least one conveyance mechanism coupled to the base allowing the low-field MR device to be transported to different locations;
at least one electrophysiological device; and
at least one controller configured to operate the low-field MR device to obtain MR data and to operate the at least one electrophysiological device to obtain electrophysiological data.

2. The system of claim 1, wherein the at least one electrophysiological device comprises an electroencephalography (EEG) device comprising a plurality of electrodes configured to obtain EEG data while a patient is within a field of view of the low-field magnetic resonance device, and wherein the at least one controller is configured to operate the EEG device to obtain the EEG data.

3. The system of claim 2, wherein the at least one controller is configured to adapt at least one characteristic of the low-field magnetic resonance device based, at least in part, on the EEG device.

4. The system of claim 3, wherein the at least one controller is configured to adapt at least one characteristic of the low-field magnetic resonance device based, at least in part, on the EEG data.

5. The system of claim 4, wherein the at least one controller is configured to change a field of view of an MR acquisition process based on the EEG data.

6. The system of claim 4, wherein the at least one controller is configured to change a signal-to-noise ratio of an MR acquisition process based on the EEG data.

7. The system of claim 4, wherein the at least one controller is configured to change a resolution of an MR acquisition process based on the EEG data.

8. The system of claim 2, wherein the EEG device is operably connected to the low-field magnetic resonance device by at least one communications connection.

9. The system of claim 1, wherein the magnetics components are configured to produce the $B_0$ field having a strength equal to or less than 0.1 T and greater than or equal to 50 mT.

10. The system of claim 1, wherein the base is further configured to support the at least one electrophysiological device such that the system can be transported and operated in different locations.

11. The system of claim 10, wherein the system is configurable in a configuration for transporting the system and a configuration for operating the system.

12. The system of claim 1, wherein the low-field magnetic resonance device is configured to generate an MR image having an in-plane resolution of at least three millimeters and up to and including one millimeter.

13. The system of claim 1, wherein the low-field magnetic resonance device is configured to generate an MR image having a resolution up to and including three millimeters isotropic.

14. The system of claim 1, wherein the controller is configured to operate the low-field MR device and the electrophysiological device to obtain the MR data and the electrophysiological data while a patient remains in a field of view of the low-field MR device.

15. The system of claim 1, wherein the at least one controller is configured to operate the low-field magnetic resonance device and the at least one electrophysiological device simultaneously.

16. The system of claim 1, wherein the at least one power component configured to provide power to the first and second laminate panels comprises at least one gradient coil amplifier.

17. A method of operating a system comprising at least one electrophysiological device and a low-field magnetic resonance (MR) device comprising a magnetics system having a plurality of magnetics components configured to produce magnetic fields for performing magnetic resonance imaging, the magnetics system comprising a $B_0$ magnet configured to produce a $B_0$ field for an imaging region of the low-field MR device, the $B_0$ magnet comprising at least one first $B_0$ magnet and at least one second $B_0$ magnet positioned in a bi-planar arrangement about the imaging region, and at least one laminate panel, a power system comprising one or more power components configured to provide power to the magnetics system to operate the low-field MR device to perform image acquisition, the one or more power components comprising at least one power component configured to provide power to the at least one laminate panel, a base that supports the magnetics system and houses the power system, and at least one conveyance mechanism coupled to the base allowing the low-field MR device to be transported to different locations, the method comprising:
  while a patient is positioned within a field of view of the low-field MR device:
    operating the low-field magnetic resonance device to obtain MR data using the at least one laminate panel, the laminate panel comprising a plurality of laminate layers, each of the plurality of laminate layers including at least one non-conductive layer and at least one conductive layer patterned to form at least a portion of a gradient coil configured to produce at least a portion of a gradient magnetic field, wherein the at least one laminate panel comprises a first laminate panel comprising a first gradient coil and a second laminate panel comprising a second gradient coil, the first and second gradient coils of the first and second laminate panels being disposed on opposite sides of the imaging region; and
    operating the at one electrophysiological device to obtain electrophysiological data.

* * * * *